(12) United States Patent
Reed et al.

(10) Patent No.: US 7,716,969 B2
(45) Date of Patent: May 18, 2010

(54) METHODS AND DEVICES FOR SIMULTANEOUSLY MONITORING COLLOID PARTICLES AND SOLUBLE COMPONENTS DURING REACTIONS

(75) Inventors: Wayne F. Reed, New Orleans, LA (US); Alina M. Alb, New Orleans, LA (US); Stephen J. O'Donohue, Church Stretton (GB); Robert M. Anderson, Craven Arms (GB)

(73) Assignees: The Administrators of the Tulane Educational Fund, New Orleans, LA (US); Polymer Laboratories Ltd., Shropshire (GB)

( * ) Notice: Subject to any disclaimer, the term of this patent is extended or adjusted under 35 U.S.C. 154(b) by 0 days.

(21) Appl. No.: 11/865,589

(22) Filed: Oct. 1, 2007

(65) Prior Publication Data

US 2008/0216563 A1    Sep. 11, 2008

Related U.S. Application Data

(60) Provisional application No. 60/827,559, filed on Sep. 29, 2006, provisional application No. 60/884,821, filed on Jan. 12, 2007.

(51) Int. Cl.
G01N 15/06    (2006.01)

(52) U.S. Cl. .................................................... 73/61.71
(58) Field of Classification Search ............... 73/61.71, 73/865.5; 356/335, 336, 338; 436/164, 166, 436/179
See application file for complete search history.

(56) References Cited

U.S. PATENT DOCUMENTS

| | | | | |
|---|---|---|---|---|
| 4,226,114 A | * | 10/1980 | Hagedorn | .................. 73/61.76 |
| 6,052,184 A | | 4/2000 | Reed | |
| 6,618,144 B1 | | 9/2003 | Reed | |
| 6,653,150 B1 | | 11/2003 | Reed | |
| 2004/0004717 A1 | | 1/2004 | Reed | |

* cited by examiner

*Primary Examiner*—John Fitzgerald
(74) *Attorney, Agent, or Firm*—Garvey, Smith, Nehrbass & North, L.L.C.; Seth M. Nehrbass; Charles C. Garvey, Jr.

(57) ABSTRACT

A method and apparatus for continuously extracting liquid in at least two separate streams from a vessel, continuously diluting and/or conditioning a first stream in one or more stages, producing, as a result of the extraction, dilution and/or conditioning, the first stream consisting of a dispersion of particles to be characterized, and diluting and/or conditioning a second stream, the second stream consisting of soluble components; and subjecting the first and second streams to various characterizing measurements.

20 Claims, 32 Drawing Sheets

Multiple withdrawal tubes

Pumps 30

METHODS AND DEVICES FOR SIMULTANEOUSLY MONITORING COLLOID PARTICLES AND SOLUBLE COMPONENTS DURING REACTIONS

CROSS-REFERENCES TO RELATED APPLICATIONS

U.S. Provisional Patent Application Ser. No. 60/827,559, filed 29 Sep. 2006, and U.S. Provisional Patent Application Ser. No. 60/884,821, filed 12 Jan. 2007, priority of both of which is hereby claimed, are hereby incorporated herein by reference.

STATEMENT REGARDING FEDERALLY SPONSORED RESEARCH

Not Applicable.

REFERENCE TO "MICORFICHE APPENDIX"

Not Applicable.

BACKGROUND OF THE INVENTION

1. Field of the Invention

The present invention relates to the simultaneous characterization of microscopic particles in suspension and soluble components diluted in a different fluid.

2. General Background of the Invention

Polymerization reactions in heterogeneous phase are widely used in industry, and comprise many tens of billions of dollars per year in production, worldwide. The present invention involves polymers produced in heterogeneous phases such as micelles, miniemulsions, macroemulsions, suspensions, and the latex particles that result. The term "emulsion polymerization reactions" (EPR) includes polymers produced in heterogeneous phases such as micelles, miniemulsions, macroemulsions, suspensions, and the latex particles that result, as well as inverse micelles, inverse miniemulsions, and inverse macroemulsions. The term "particle" used in the context of "particle characterization" includes, but is not limited to, for example, micelles, latex particles, aggregates, emulsions, inverse micelles, inverse emulsions, and miniemulsions.

Strong economic and environmental motivations are fueling a growing trend toward making more use of EPR: EPR reduces the use of dangerous organic solvents (EPR are normally carried out in water, whereas inverse phases are usually carried out in oils), EPR allows better control of thermodynamics (exothermicity), and the emulsion liquids used in EPR have low viscosity and are easy to handle, pump, transport, store, and apply. Furthermore, the latex particles produced by EPR often have desirable end products, for example, paints, coatings, and adhesives.

As in any process where a particular composition of matter is sought through chemical reactions (covalent), including biochemical reactions, as well as physical (non-covalent) interactions of initial substances, entities (e.g. cells), and reagents, it is inherently valuable to be able to monitor the changes that occur in realtime or near realtime.

In general, there are many advantages to being able to monitor such reactions. Monitoring gives a fundamental understanding of the reaction kinetics and mechanisms, and the evolution of polymer properties (such as molecular weight) during synthesis, allowing the development of advanced polymeric materials. Monitoring gives the ability to optimize reaction conditions, including, for example, pressures, temperatures, reagents, monomers, activators, catalysts, process steps and stages, and also yields the ability to provide full control of large scale production of polymers, biopolymers, and other substances. Such control leads to novel and superior products, better quality control, more efficient use of natural and non-renewable resources, energy, and plant and personnel time.

In the case of EPR, the advantages of accurate comprehensive monitoring of the reactions leads to optimized latex particles using particle characterization, whereas monitoring the soluble components in a separate analysis stream can allow quantification of conversion of reagents, such as monomers and comonomers, thus allowing the personnel involved to know at what stage the reaction is, whether the reaction is functioning correctly, when it is time to add new or different reagents, how to change the flow of reagents in continuous or semi-batch reactors, when to perform other actions affecting the reaction, such as changing temperature, and when to stop the reaction. Monitoring the soluble components also allows the evolution of polymeric properties to be followed, for example, average molar masses, intrinsic viscosity, the degree of polymer branching and the degree of polymer grafting. The type of simultaneous monitoring disclosed herein leads to such a better fundamental understanding of the complex processes involved in EPR that new procedures may be developed, and/or redundant or counterproductive steps in old procedures may be identified and/or eliminated.

There has been, and continues to be, much effort expended to monitor EPR, but the focus for particle characterization has usually been on manually withdrawing discrete aliquots and making particle size measurements, usually with dynamic light scattering (DLS). Monomer conversion is separately measured by drying and weighing discrete samples, or by other means, such as Gel Permeation Chromatography (GPC), often also referred to as Size Exclusion Chromatography (SEC). Another growing area for monitoring monomer conversion involves in-situ reactor probes of near infra-red, Raman scattering, ultrasound, and calorimeters. These processes, while providing continuous automatic signals, give only empirical information about changes in the reaction, require empirical or inferential calibration schemes, can contain signals from other effects that obscure the useful portion of the signal (e.g. scattering by emulsions rather than absorption by monomers can dominate spectroscopic signals using electromagnetic probe radiation) and are directly subject to often harsh reactor interiors that leads to rapid fouling, failure of calibration, and instrument malfunction.

The disadvantage of manually withdrawing discrete aliquots and making particle size measurements, often with DLS, is that it is labor intensive, inefficient, slow, potentially dangerous to personnel, and also risks contamination in the reaction vessel. Some progress has been made, nonetheless, in automatic dilution of emulsion reactor contents for particle sizing measurements by DLS and combined low, mid, and high angle light scattering, notably by Malvern Ltd. of the UK.

The disadvantage to monitoring monomer conversion by separately drying and weighing discrete samples, or by other means, is that it is time consuming, labor intensive, and only yields few conversion points, with a very long delay between withdrawal and measurement. This is suitable neither for reactor control nor for fundamental studies of reaction kinetics.

The disadvantage of the in-situ probes is that they are subject to harsh conditions, can easily foul or be damaged, deliver limited information (e.g. only conversion), and are predicated on empirical or inferential models that quickly change as reactor conditions and probe conditions change.

There does not seem to be any precedent in the field for a device or method which simultaneously and automatically measures both colloid and polymer/monomer aspects of EPR.

Incorporated herein by reference are all patents and patent applications naming one or more of the inventors herein as an inventor, and all publications listing one or more of the inventors as an author, including the following: International Publication No. WO01/29534 A1, US Patent Publication No. US 2004/0004717, U.S. Pat. No. 6,653,150, U.S. Pat. No. 6,618,144, and U.S. Pat. No. 6,052,184.

Also incorporated herein by reference are the following publications: F. H. FLORENZANO, R. STRELITZKI, W. F. REED, "Absolute, Online Monitoring of Polymerization Reactions", *Macromolecules,* 31, 7226-7238, 1998; R. STRELITZKI, W. F. REED, "Automated Batch Characterization of Polymer Solutions by Static Light Scattering and Viscometry", *J. App. Polym. Sci.,* 73, 2359-2368 1999; R. SCHIMANOWSKI, R. STRELITZKI, D. A. MULLIN, W. F. REED "Heterogeneous Time Dependent Static Light Scattering", *Macromolecules,* 32, 7055-7063, 1999; J-L BROUSSEAU, H. ç. GIZ, W. F. REED, "Automatic, Simultaneous Determination of Differential Refractive Index of a Polymer and its Corresponding Monomer", *J. App. Polym. Sci.,* 77, 3259-3262, 2000; W. F. REED, "A Method for Online Determination of Polydispersity during Polymerization Reactions", *Macromolecules,* 33, 7165-7172, 2000; E. BAYLY, J. L. BROUSSEAU, W. F. REED, "Continuous Monitoring of the Effect of Changing Solvent Conditions on Polyelectrolyte Conformations and Interactions", *Int. J. of Polymer Characterization and Analysis,* 7, 1-19, 2002; A. GIZ, H. GIZ, J. L. BROUSSEAU, A. ALB, and W. F. REED, "Kinetics and Mechanism of Acrylamide Polymerization by Absolute, Online Monitoring of Polymerization Kinetics", *Macromolecules,* 34, 5, 1180-1191, 2001; A. GIZ, H. GIZ, J. L. BROUSSEAU, A. ALB, W. F. REED, "Online Monitoring of a Stepwise Polymerization Reaction: Polyurethane", *J. App. Polym. Sci.,* 82, 2070-2077, 2001; J. L. GANTER, W. F. REED, "Real-time Monitoring of Enzymatic Hydrolysis of Galactomannans", *Biopolymers,* 59, 226-242, 2001; B. GRASSL, A. M. ALB, W. F. REED, "Free radical transfer rate determination using online polymerization monitoring", *Macromolecular Chemistry and Physics,* 202, 2518-2524, 2001; G. A. SORCI, W. F. REED, "Electrostatic and Association Phenomena in Aggregates of Polymers and Micelles", *Langmuir,* 18, 353-364, 2002; B. GRASSL, W. F. REED, "Online polymerization monitoring in a continuous tank reactor", *Macromolecular Chemistry and Physics,* 203, 586-597, 2002; F. CHAUVIN, A. M. ALB, D. BERTIN, W. F. REED, "Kinetics and molecular weight evolution during controlled radical polymerization", *Macromolecular Chemistry and Physics,* 203, 2029-2040, 2002; G. A. SORCI, W. F. REED, "Electrostatically enhanced second and third virial coefficients, viscosity and interparticle correlations for linear polyelectrolytes", *Macromolecules,* 35, 5218-5227, 2002; A. GIZ, A. Oncul KOC, H. GIZ, A. M. ALB, W. F. REED "Online monitoring of reactivity ratios, composition, sequence length, and molecular weight distributions during free radical copolymerization", *Macromolecules,* 35, 6557-6571, 2002; W. F. REED, "Monitoring Kinetic Processes in Polymer Solutions with Time Dependent Static Light Scattering (TDSLS)", Ch. 12, pp. 131-151, in *Scattering Methods for the Investigation of Polymers,* J. Kahovec, Ed., Wiley VCH, 2002; W. F. REED, A. M. ALB, E. MIGNARD, H. GIZ, A. GIZ, F. H. FLORENZANO, R. FARINATO "Automatic Continuous Online Monitoring of Polymerization Reactions (ACOMP)", *Polymeric Materials: Science and Engineering,* 88, 476-478, 2003; M. F. DRENSKI, W. F. REED, "Simultaneous Multiple Sample Light Scattering (SMSLS)", *Polymeric Materials: Science & Engineering,* 88, 304-305, 2003; E. MIGNARD, O. GUERRET, D. BERTIN, W. F. REED, "Automatic Continuous Online Monitoring of Polymerization Reactions (ACOMP) of High Viscosity Reactions", *Polymeric Materials: Science and Engineering,* 88, 314-316, 2003; W. F. REED, "Automatic, Continuous Mixing Techniques for Online Monitoring of Polymer Reactions and for the Determination of Equilibrium Properties", *Ch.* 20, 589-622, *Handbook of Size Exclusion Chromatography and Related Techniques,* $2^{nd}$ Ed., Chi-san Wu, Ed., Marcel Dekker, 2003; H. çATALGIL-GIZ, A. GIZ, A. M. ALB, W. F. REED, "Absolute Online Monitoring of Acrylic acid Polymerization and the Effect of Salt and pH on Reaction Kinetics", *J. Applied Polymer Science,* 91, 1352-1359, 2004; G. A. SORCI, W. F. REED, "Effect of valence and chemical species of added electrolyte on polyelectrolyte conformations and interactions", *Macromolecules,* 37, 554-565, 2004; E. MIGNARD, T. LEBLANC, D. BERTIN, O. GUERRET, W. F. REED, "Online monitoring of controlled radical polymerization: Nitroxide mediated gradient copolymerization", *Macromolecules,* 37, 966-975, 2004; W. F. REED, "Fundamentals of static light scattering and viscometry in SEC and related methods", ACS Ser. 893 *Multiple Detection Size-Exclusion Chromatography,* A. M. Striegel, Ed., ACS: Washington, D.C., 2004; W. F. REED, "Automatic Continuous Online Monitoring of Polymerization reactions (ACOMP)", *Polymer News,* 29, 271-279, 2004; M. F. DRENSKI, W. F. REED, "Simultaneous Multiple Sample Light Scattering for Characterization of Polymer Solutions", *J. App. Polym. Sci., vol.* 92, 2724-2732, 2004; A. M. ALB, E. MIGNARD, M. F. DRENSKI, W. F. REED, "In Situ Time dependent signatures of light scattered from solutions undergoing polymerization reactions", *Macromolecules,* 37, 2578-2587, 2004; M. F. DRENSKI, E. MIGNARD, A. M. ALB, W. F. REED, "Simultaneous in Situ Monitoring of Parallel Polymerization Reactions using Light Scattering; a New Tool for High Throughput Screening", *J. Combinatorial Chemistry,* 6, 710-716, 2004; F. H. FLORENZANO, V. FLEMING, P. ENOHNYAKET, W. F. REED, "Coupling of Near Infra-Red spectroscopy to Automatic Continuous Online Monitoring of Polymerization Reactions", *European Polymer Journal,* 41, 535-545, 2005; R. S. FARINATO, J. CALBICK, G. A. SORCI, F. H. FLORENZANO, W. F. REED, "Online monitoring of the final divergent growth phase in the stepgrowth polymerization of polyamines" *Macromolecules,* 38, 1148-1158, 2005; E. MIGNARD, J-F LUTZ, T. LEBLANC, K. MATYJASZEWSKI, O. GUERRET, W. F. REED, "Kinetics and Molar Mass Evolution during Atom Transfer Radical Polymerization of n-Butyl Acrylate Using Automatic Continuous Online Monitoring." *Macromolecules,* 38, 9556-9563, 2005; A. M. ALB, R. FARINATO, J. CALBECK, W. F. REED, "Online monitoring of polymerization reactions in inverse emulsions", *Langmuir,* 22, 831-840, 2006; A. M. ALB, P. ENOHNYAKET, M. DRENSKI, A. HEAD, A. W. REED, W. F. REED, "Online monitoring of copolymerization using comonomers of similar spectral characteristics", *Macromolecules,* 39, 5705-5713, 2006; A. M. ALB, P. ENOHNYAKET, R. SHUNMUGAM, G. N. TEW, W. F. REED, "Quantitative contrasts in the copolymerization of acrylate and methacrylate monomers", *Macromolecules,* 39, 8283-8292, 2006; M. F. DRENSKI, E. MIGNARD, W. F. REED, "Direct Measurement of Chain Transfer during Controlled Radical Polymerization", *Macromolecules,* 39, 8213-8215, 2006; A. M. ALB, P. ENOHNYAKET, J. F. CRAYMER, T. EREN, E. B. COUGHLIN, W. F. REED, "Online monitoring of Ring Opening Metathesis Polymerization of Cyclooctadiene and a Functionalized Norbornene", *Macromolecules,* 40, 444-451, 2007; A. M. ALB, A. PARIL, H. çATALGIL-GIZ, A. GIZ, W. F. REED, "Evolution of composition, molar mass, and conductivity during the free radical copolymerization of polyelectrolytes", *J. Phys. Chem. B.,* 111, 8560-8566, 2007; A. PARIL, A. M. ALB, W. F. REED, "Online Monitoring of the Evolution of Polyelectrolyte Characteristics during Postpolymerization Modification Processes", *Macromolecules,* 40, 4409-4413, 2007;

BRIEF SUMMARY OF THE INVENTION

The present invention is preferably a device for determining characteristics of a dispersion of particles and of soluble components of a liquid in a vessel, comprising, an extracting means for continuously extracting a first stream and a second stream of the liquid from the vessel, a first dilution/conditioning means for continually diluting and/or conditioning the first stream in one or more stages, whereby the diluted and/or conditioned first stream facilitates characterization of the dispersion of the particles, a second dilution/conditioning means for diluting and/or conditioning the second stream whereby the diluted and/or conditioned second stream facilitates characterization of the soluble components, a particle characterizing means for characterizing the particles, and a component characterizing means for characterizing the soluble components.

The present invention is preferably a device for determining characteristics of a dispersion of particles and of soluble components of a liquid in a vessel in which a reaction, involving polymer and/or dispersed particles, occurs, comprising, an extracting means for simultaneously extracting a first stream and a second stream of the liquid from the vessel, whereby the extraction is continuous, a first dilution/conditioning means for continually diluting and/or conditioning the first stream in one or more stages, whereby the diluted and/or conditioned first stream facilitates characterization of the dispersion of the particles, a second dilution/conditioning means for diluting and/or conditioning the second stream whereby the diluted and/or conditioned second stream facilitates characterization of the soluble components related to the reaction in the vessel, such as monomers, comonomers, polymer chains, and fragments of polymers, a particle characterizing means for characterizing the dispersion of the particles, and a component characterizing means for characterizing the soluble components.

In a preferred embodiment of the present invention samples are collected in sample vials for subsequent measurements of any type from the first stream prior to or subsequent to dilution and/or conditioning or from the second stream prior to or subsequent to dilution and/or conditioning.

In a preferred embodiment of the present invention the liquid extracted from the vessel is from a polymerization reaction occurring in an emulsion or an inverse emulsion phase. If the liquid is an emulsion, the emulsion may be partially or fully stabilized by a surfactant or combination of surfactants or may not be stabilized by any surfactant. The emulsion may be a miniemulsion if it is a surfactant-stabilized emulsion, or the emulsion may be a macroemulsion if the emulsion partially stabilized by surfactant.

The present invention preferably may include a single tube, or two or more tubes, for extracting the first stream from the vessel and a dividing means for subsequently dividing the first stream into at least a primary tributary stream and a secondary tributary stream. An alternative preferred embodiment may include two or more tributary tubes or capillaries connected to a single tube. Another preferred embodiment of the present invention provides two or more tubes, one of which separately connects to two or more tributary tubes or capillaries. A further embodiment of the present invention provides tubes communicating with the vessel for separately extracting the first stream and the second stream. Each tributary tube or capillary may have an internal diameter which may be comparable to each other or may vary by up to a factor of 100. In an alternative preferred embodiment, the flow rate of each tributary stream is controlled by microfluidic controllers.

In one preferred embodiment of the present invention, the first stream contains a dispersion of particles. In another preferred embodiment of the present invention, the first stream is subjected to at least one characterizing measurement for example, a particle characterizing measurement. In yet another preferred embodiment of the present invention, the particle characterizing means may include particle size distribution determining means, average of the particle size distribution determining means, particle number density measuring means, particle chemical composition determining means, particle shape and morphology determining means, particle structure measuring means. The characterizing measurement of the present invention may be continuous or non-continuous and may utilize flow injection.

In another preferred embodiment of the present invention, particle fractionation occurs prior to determining particle characteristics and the particle fractionation may be from the group consisting of gel permeation chromatography, field flow fractionation (including temperature, gravity, differential flow fields, centrifugal fields), capillary hydrodynamic fractionation, size exclusion chromatography. The characterizing measurement of the present invention may be obtained from one or more particle characterizing instruments which measure light scattering, electric zone sensing, change in dielectric constant, turbidity, conductivity, and/or infra red measurements of the dispersion of the particles.

In an alternative embodiment of the present invention, the liquid extracted from the vessel is from a reaction involving biopolymers, or processes involving biopolymer extraction from biological cells. A further embodiment provides for a first stream including a dispersion of cells, cell organelles, cell clusters, or cell fragments, and wherein at least one other stream including soluble cellular extracts or exudates.

In one preferred embodiment of the present invention, the second stream further comprises solubilized components. In another preferred embodiment of the present invention, the second stream further comprises dissolved components of a polymer reaction from the group consisting of monomers, polymers, and polymer fragments, catalysts, initiators, chelating agents, stabilizing agents, surfactants, salts, and other small (non-polymeric) molecules. In another preferred embodiment of the present invention, the second stream may be subjected to at least one characterizing measurement, for example, a polymer or monomer characterizing measurement. In yet another preferred embodiment of the present invention, the characterizing measurement may be a single monomer concentration determining means, from which kinetics of monomer conversion into the polymer is determined. In an alternative preferred embodiment of the present invention, the component characterizing means may include average molar mass measuring means, mass distribution measuring means, polymer size detecting means, polymer hydrodynamic dimension detection means, polymer intrinsic viscosity measuring means, degree of polymer branching measuring means, degree of polymer cross-linking measuring means, determination of copolymer chemical composition means, determination of copolymer chemical sequence means, degree of micellization means, and degree of chemical modification means. The characterizing measurement of the present invention may be obtained from one or more characterizing instruments which measure light scattering, viscosity, refractive index, conductivity, nuclear magnetic resonance, electron spin resonance, ultra-violet, visible, or infra-red absorbance, fluorescence, luminescence, of the soluble component.

One embodiment of the present invention provides that the first stream may be diluted at least ten times more than the second stream. In one embodiment, the first dilution/conditioning means of the present invention may be water. Alternatively, the first dilution/conditioning means may be an aqueous solution comprising any one or a combination of added electrolytes, surfactants, electrolytes, chelating agents, or other organic or aqueous liquids. In a further alternative embodiment, the first dilution/conditioning means stream is an organic solvent, or a mixture of organic solvents, or a mixture of organic solvent and water, or a mixture of organic solvents and water. In yet a further alternative embodiment, the composition diluent changes over time.

In one embodiment of the present invention provides that the second dilution/conditioning means is water. Alternatively, the second dilution/conditioning means is an aqueous solution comprising any single one or combination of added electrolytes, surfactants, electrolytes, chelating agents, or other organic or aqueous liquids. In a further alternative embodiment, the second dilution/conditioning means is an organic solvent or a mixture of organic solvent and water.

The present invention may further include a comonomer concentration determining means when the component characterizing means may be a measuring means for measuring: the concentration of each comonomer, polymer composition drift during the reaction, average copolymer composition distribution, average copolymer composition distribution including end product distribution, or reactivity ratios of the comonomers.

In an alternative embodiment of the present invention, the first stream may be measured by the particle characterization means without dilution or conditioning. In yet another alternative embodiment of the present invention, the first stream is measured by the particle characterization detector without dilution.

The soluble components of the present invention may be biopolymers.

In another preferred embodiment, the present invention includes a recirculation loop, and the streams may be extracted from the vessel via the recirculation loop.

A further preferred embodiment of the present invention includes a means for conducting packed column hydrodynamic chromatography on one of the streams.

Another preferred embodiment of the present invention further includes a filtration means for filtering at least one of the streams. The filtration means may be at least one means from the group consisting of point of extraction and in-line filtration using membranes, glass wool, frits, sintered glass or other sintered materials.

The present invention may include a fractionation means for the soluble component stream, comprising at least one means from the group consisting of GPC, SEC, MALDI-TOF, field flow fractionation, and capillary hydrodynamic fractionation.

The present invention is preferably a method for determining characteristics of a dispersion of particles and of soluble components of a liquid in a vessel, including the steps of continuously extracting a first stream and a second stream of the liquid from the vessel, the step of continually diluting and/or conditioning the first stream in one or more stages, whereby the diluted and/or conditioned first stream facilitates characterization of the dispersion of the particles, the step of diluting and/or conditioning the second stream whereby the diluted and/or conditioned second stream facilitates characterization of the soluble components, the step of characterizing the particles, and the step of characterizing the soluble components.

The present invention is preferably a method for determining characteristics of a dispersion of particles and of soluble components of a liquid in a vessel in which a reaction, involving polymer and/or dispersed particles, occurs, including the step of simultaneously extracting a first stream and a second stream of the liquid from the vessel, whereby the extraction is continuous, the step of continually diluting and/or conditioning the first stream in one or more stages, whereby the diluted and/or conditioned first stream facilitates characterization of the dispersion of the particles, the step of diluting and/or conditioning the second stream whereby the diluted and/or conditioned second stream facilitates characterization of the soluble components related to the reaction in the vessel, such as monomers, comonomers, polymer chains, and fragments of polymers, the step of characterizing the dispersion of the particles, and the step of characterizing the soluble components.

In a preferred embodiment of the present invention the step of collecting samples in sample vials for subsequent measurements of any type from the first stream prior to or subsequent to dilution and/or conditioning or from the second stream prior to or subsequent to dilution and/or conditioning.

In a preferred embodiment of the present invention the liquid extracted from the vessel is from a polymerization reaction occurring in an emulsion or an inverse emulsion phase. If the liquid is an emulsion, the present invention may further include the step of stabilizing or partially stabilizing the emulsion with a surfactant or combination of surfactants. In another embodiment of the present invention, the emulsion may not be stabilized by any surfactant. The emulsion may be a miniemulsion if it is a surfactant-stabilized emulsion, or the emulsion may be a macroemulsion if the emulsion partially stabilized by surfactant.

The present invention preferably may include the step of extracting each of the at least two streams through its own tube that communicates with the vessel. An alternative preferred embodiment may include the step of extracting the first stream from the vessel through a single tube and subsequently dividing the first stream into at least a primary tributary stream and a secondary tributary stream. A further embodiment includes the step of connecting the single tube to at least two tributary tubes or capillaries. Each tributary tube or capillary may have an internal diameter which may be comparable to each other or may vary by up to a factor of 100. Another preferred embodiment of the present invention includes performing said first stream extracting step with at least two separate tubes and connecting at least one of those tubes to at least two smaller diameter tubes. Another preferred embodiment of the present invention includes controlling flow rates of each tributary stream with microfluidic controllers.

In one preferred embodiment of the present invention, the first stream contains a dispersion of particles. Another preferred embodiment of the present invention includes the step of subjecting the first stream to at least one characterizing measurement. A further preferred embodiment includes determining a particle characterizing measurement. In yet another preferred embodiment of the present invention, the determining step may include determining the particle size distribution, determining the average of the particle size distribution, measuring the particle number density, determining the particle chemical composition, determining the particle shape and morphology, or measuring the particle structure. The determining step of the present invention may be continuous or non-continuous and, if non-continuous, may utilize flow injection.

In another preferred embodiment of the present invention, the step of particle fractionation occurs prior to step of determining particle characteristics and the particle fractionation step may include gel permeation chromatography, field flow fractionation (including temperature, gravity, differential flow fields, centrifugal fields), capillary hydrodynamic fractionation, or size exclusion chromatography. The present invention may further include the step of measuring light scattering, electric zone sensing, change in dielectric constant, turbidity, conductivity, and/or infra red measurements of the dispersion of the particles.

In an alternative embodiment of the present invention, the liquid extracted from the vessel is from a reaction involving biopolymers, or processes involving biopolymer extraction from biological cells. A further embodiment provides for a first stream including a dispersion of cells, cell organelles, cell clusters, or cell fragments, and wherein at least one other stream including soluble cellular extracts or exudates.

In one preferred embodiment of the present invention, the second stream further comprises solubilized components. The second stream may further comprise dissolved components of a polymer reaction from the group consisting of monomers, polymers, and polymer fragments, catalysts, initiators, chelating agents, stabilizing agents, surfactants, salts, and other small (non-polymeric) molecules. Another preferred embodiment of the present invention includes the step of subjecting the second stream to at least one characterizing measurement. A further preferred embodiment includes determining a polymer or monomer characterizing measurement. A further preferred embodiment of the present invention may include the step of determining the concentration of a single monomer, and further include the step of determining kinetics of monomer conversion into polymer. An alternative preferred embodiment of the present invention may include the step of determining the concentration of two or more comonomers, and the step of measuring polymer composition drift during the reaction, average copolymer composition distribution at any moment of the distribution, including of end product distribution, and/or reactivity ratios of the comonomers. Another embodiment of the present invention may include the step of measuring average molar mass, the step of measuring mass distribution, the step of detecting polymer size, the step of detecting polymer hydrodynamic dimension, the step of measuring polymer intrinsic viscosity, the step of measuring degrees of polymer branching, and/or the step of measuring degrees of polymer cross-linking. Another preferred embodiment of the present invention may include the step of measuring light scattering, viscosity, refractive index, conductivity, ultra-violet, visible, and/or infra-red absorbance.

One preferred embodiment of the present invention includes the step of diluting the first stream at least ten times more than the second stream. In one embodiment, the first stream diluting step may be water. Alternatively, the first stream diluting step may be an aqueous solution comprising any one or a combination of added electrolytes, surfactants, electrolytes, chelating agents, or other organic or aqueous liquids. Alternatively, the first stream diluting step may be organic solvent or a mixture of organic solvent and water.

Another embodiment of the present invention includes the second stream diluting step may be organic solvent, or a mixture of organic solvents, or a mixture of organic solvent and water, or a mixture of organic solvents and water. Alternatively, the second stream diluting step may be water. Alternatively, the second stream diluting step may be an aqueous solution comprising any one or a combination of added electrolytes, surfactants, electrolytes, chelating agents, or other organic or aqueous liquids. In a further alternative embodiment, the second stream diluting step may be an organic solvent or a mixture of organic solvent and water.

In one preferred embodiment of the present invention, the soluble components may be biopolymers.

In another preferred embodiment, the present invention includes the step of extracting the streams from the vessel via a recirculation loop.

A further preferred embodiment of the present invention includes the step of conducting packed column hydrodynamic chromatography on one of the streams.

In another preferred embodiment, the present invention includes the step of subjecting the second stream to at least one interrupted measurement.

Another preferred embodiment of the present invention further includes the step of filtering at least one of the streams.

The present invention may include a fractionation step for the soluble component stream, comprising at least one means from the group consisting of GPC, SEC, MALDI-TOF, field flow fractionation, and capillary hydrodynamic fractionation.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
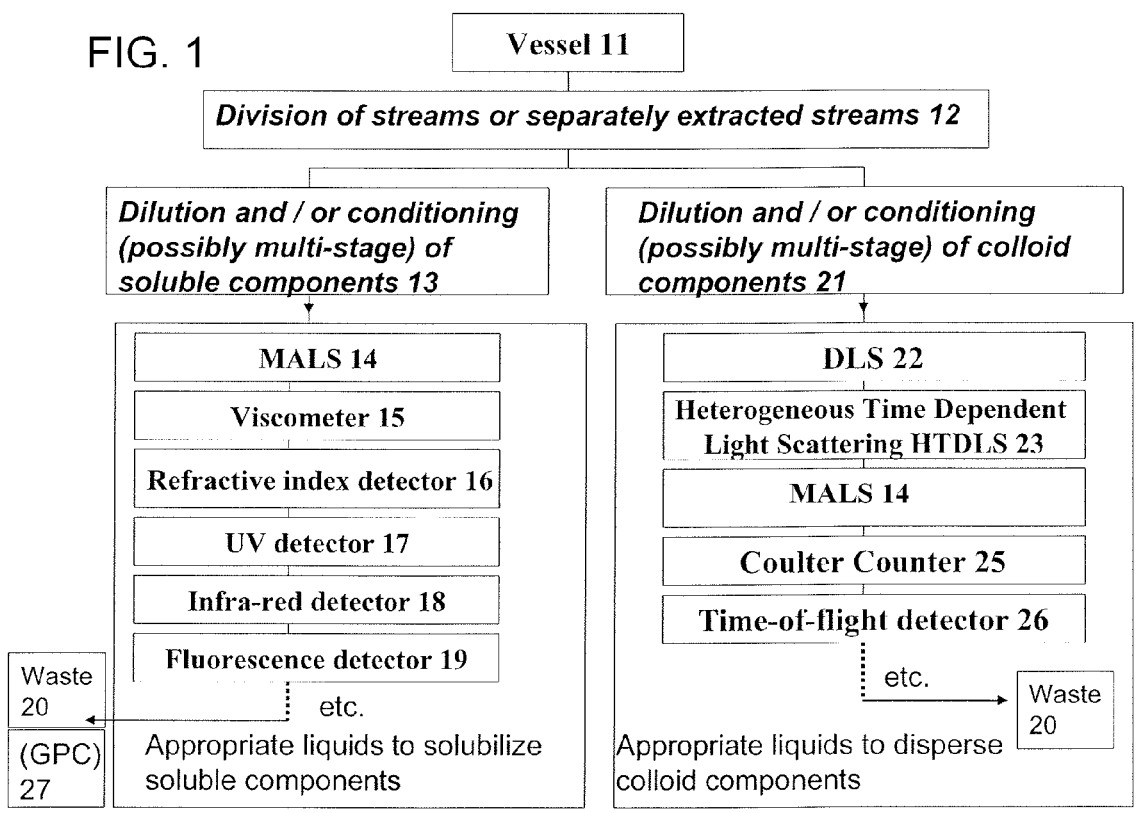
FIG. 1 is a schematic flow chart of a preferred embodiment of the apparatus of the present invention.
Figure 2:
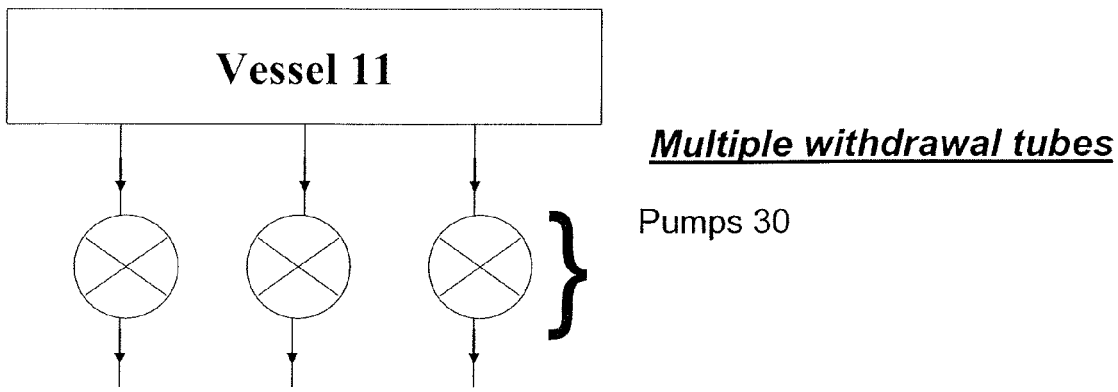
FIG. 2 is an alternate preferred embodiment of the apparatus of the present invention.
Figure 3:
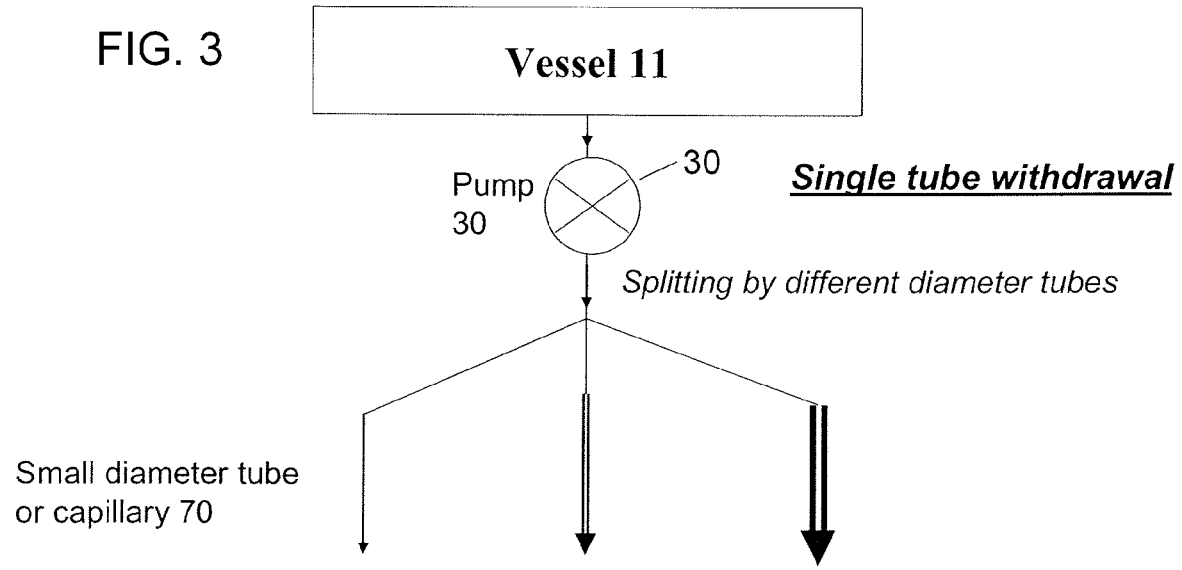
FIG. 3 is an alternate preferred embodiment of the apparatus of the present invention.

Detailed descriptions of one or more preferred embodiments are provided herein. It is to be understood, however, that the present invention 10 may be embodied in various forms. Therefore, specific details disclosed herein are not to be interpreted as limiting, but rather as a basis for the claims and as a representative basis for teaching one skilled in the art to employ the present invention 10 in any appropriate system, structure, or manner.

In principle, the size range of detectability of the colloids should run from about 20 Angstroms to 500 microns, with useful measurability in the range from 20 Angstroms to 100 microns, and a preferred range from about 20 Angstroms to 100,000 Angstroms. Stated in terms of molar mass, the detectable range of particles should run from about $10^7$ g/mole to $10^{15}$ g/mole. The range of detection of the polymer/monomer and other soluble components includes small, monomeric structures (for example styrene, butyl acrylate, acrylamide) as well as polymers with useful measurability in the range of 50 g/mole to $10^9$ g/mole, with a preferred range from about 50 g/mole to $10^7$ g/mole.

The present invention 10, which is preferably fully automatic, overcomes the limitations of existing monitoring methods and devices and provides, simultaneously, the most accurate characterization of both the microscopic particles in suspension and soluble component characteristics of the EPR. The present invention 10 contributes to the efficiency and productivity of various processes, including polymerization. The present invention 10 reduces environmental concerns associated with large-scale polymerization reactions by making the use of EPR more efficient. The present invention 10 provides a fundamental, unified understanding of the many complex characteristics, processes and phenomena involved in EPR, allowing for the development of new products, processes, and compositions of matter, as well as optimization of existing products at the bench and pilot plant levels. Implemented on full scale industrial reactors, the present invention 10 provides wide ranging benefits, including superior products and quality control, and more efficient use of petroleum-based resources, non-renewable resources, energy, plant, and personnel time.

The present invention 10 relates to the characterization of microscopic particles in suspension (e.g. emulsions and inverse emulsions, latex particles, microgels, and other colloid particles) and, separately and simultaneously, of soluble components diluted in a different fluid. Microscopic particles can be measured undiluted in some cases, or be diluted by an aqueous or other polar solvent in the case of organic phase droplets in water, thus conserving the particle nature. In the case of aqueous droplets in a continuous organic phase, the dilution would be made with an organic solvent that would conserve the aqueous droplets. In order to separately and simultaneously characterize the soluble components, the reactor liquid would be diluted with a fluid miscible with the continuous phase in the vessel/reactor 11, and this miscible fluid solubilizes the components. An example would be the case of organic droplets (e.g. containing monomers such as, for example, butyl acrylate, methyl methacrylate, and styrene, and corresponding polymers and copolymers thereof, as well as, for example, initiators and catalysts) in a continuous water phase diluted with an organic solvent such as tetrahydrofuran (THF) 58, which is miscible with water and solubilizes the components.

In some cases the diluent used for the particle dilution and/or the soluble component dilution 13 may consist of a mixture of pure solvents, such as mixtures of organic solvents, or water with water-miscible organic solvents, or aqueous solutions containing salts and/or surfactants, and/or chelating agents, and/or solubilizing agents, and/or other small molecules. The advantages of using mixed solvents for particle dilution is that this is sometimes the best way to conserve the particle size, shape, and other characteristics. The advantage of using mixed solvents for soluble component dilution is that sometimes this is the best way or only way to achieve the component solubility.

In other instances it can sometimes be advantageous to vary the composition of mixed solvents that are used for particle dilution and/or for polymer and soluble component dilution during the reaction. For example, when copolymers are produced whose comonomeric composition changes in time, the solubility of the copolymer can likewise change in time. Hence, varying the composition of the diluent in this case can help keep the copolymer produced in the reactor soluble in the extracted stream. Other reasons for changing the solvent composition include to induce deliberate changes in copolymer conformation and the morphology of spontaneously forming structures from copolymers. For example, some copolymers may self-organize into micelles, vesicles, fibers, cylinders or other shapes depending on solvent type and dielectric constant. It is hence possible to vary the morphology of the self-organizing structures in the continuous sample stream during the reaction by changing solvent composition.

The present invention 10, for a large class of reactions, such as polymerization in emulsions and inverse emulsions, allows for simultaneous measurement of the particle characteristics of the emulsions and the characteristics of the polymers, monomers, and other non-colloidal components. In the present invention 10, dilution of the reacting or final system by certain fluids leads to the conservation of the principal colloid characteristics, such as size, physical structure, chemical composition, and morphology, so that characterizing measurements on the colloid particle characteristics can be made, whereas in other systems it will be possible to measure colloid particle characteristics without dilution.

At the same time, in the present invention 10, dilution by different fluids leads to the solubilization of certain components, for example, monomers, initiators, polymers, and surfactants. From such a fluid comprising a dilute solution of these components, characterizing measurements on the conversion of monomers, including multiple monomers (or "comonomers") can be made, and, for example, polymer molar mass averages, distributions, intrinsic viscosity, degree of polymer branching and/or degree of polymer crosslinking can be determined. In the case of copolymers, where two or more comonomers are involved, measurement of each comonomer concentration at each instant leads to determination of average composition drift and distribution. Reactivity ratios, in the case of copolymers, can also be determined. In the solubilized stream it will be also possible, in certain cases, to measure characteristics of initiators and catalysts, for example, consumption, state of oxidation or other chemical state.

Measurement of the colloid characteristics includes size distribution, average sizes, morphology and physical structure, particle number density, chemical composition, and surface properties. Size may be measured with any number of light scattering devices (including DLS 22, or static multi-angle light scattering (MALS) 14, interpreted through diffraction, Mie, or other scattering theories (e.g. Rayleigh-Debye)), electrical zone sensing (sometimes referred to as Coulter Counting) 25, time-of-flight 26, and dielectric methods. Heterogeneous Time Dependent Static Light Scattering (HTDSLS) 23 and other methods can be used for particle number density determination. Standard analytical methods, including infra-red 18 and other spectroscopic methods can be used for chemical composition determination.

The present invention 10 allows the simultaneous characterization of colloid dispersion and soluble components, continuously and automatically with no specific limitations on the number or types of characterizing techniques that can be used. The characterization techniques themselves need not be continuous, e.g. fractionation techniques can be used, but a dilute, conditioned sample is always available to the detectors 33. One preferred embodiment of the present invention includes a particle fractionation system for detection, such as, but not limited to, capillary hydrodynamic fractionation, packed column hydrodynamic fractionation, and field flow fractionation, into which a portion of the continuous stream is periodically injected. Examples of fields that can fractionate the sample include gravity, centrifugal fields, temperature gradients, shear gradients, and electric fields. Another preferred embodiment includes fractionation of the polymer/monomer stream by periodic injection into a fractionating system such as GPC 27 or SEC. To the inventors' knowledge there is no precedent for such automatic, simultaneous characterization of EPR.

While interrupted measurements are often made in conjunction with fractionation methods such as gel permeation chromatography, size exclusion chromatography, and field flow fractionation, it is sometimes advantageous to make a non-fractionating, interrupted measurement, such as in the case of periodic or intermittent flow injection. In this a portion of the flowing stream (typically tens or hundreds of microliters) is periodically or intermittently diverted through a detector train, producing pulses of analyzable signals in each detector.

The present invention 10 encompasses methods and devices for measuring simultaneously, continuously, and automatically, both the colloid and polymer characteristics of the EPR. In the case of colloid characteristics, we refer chiefly to particle size, particle size distributions, averages of particle size distributions, particle number density, specific area, particle mass density, particle shape and morphology. These can be measured by methods such as, but not limited to, DLS 22, MALS 14 (interpreted in a variety of ways, such as, but not limited to, Mie scattering, and distributions obtained therefrom), depolarized light scattering, Diffusing Wave Spectroscopy, HTDSLS 23, electric zone sensing, conductivity, time of flight 26, and other particle characterizing methods. Sizing and other type measurements can also be made in conjunction with interrupted detection measurements on periodic diversions of the flowing stream, such as, for example, those made using field flow fractionation, and/or hydrodynamic capillary fractionation. Some of these methods involve calibrating the separation technique by particles of known sizes.

Under polymer characteristics, we refer to monomer conversion, and the evolving properties of the polymers themselves (when not cross-linked into insoluble particles during the EPR), such as, for example, molar mass M, intrinsic viscosity, and their distributions, degree of branching, and degree of grafting. When copolymers are produced using two or more species of comonomer, the method also yields the conversion kinetics of each species of comonomer, and the composition drift and distribution, in addition to the molar mass and intrinsic viscosity distributions. The present invention 10 will be applicable whether the copolymerizations involve simultaneous polymerization of two or more comonomers, or sequential polymerizations, e.g. for the production of block copolymers. Measurements made on diluted samples produced from the reactor 11 can include those made via any type of electromagnetic absorption (e.g. Ultraviolet and visible absorption, infra-red absorption), electromagnetic scattering (e.g. Raman scattering), changes in refraction, changes in chemical shifts. Examples of instruments that can make these and other types of measurements include, but are not limited to, ultraviolet and visible spectrophotometers, near infra-red spectrometers, Fourier Transform infra-red spectrometers, nuclear magnetic resonance spectrometers, electron spin resonance spectrometers, fluorescence detectors, and conductivity sensors.

Interrupted measurements on the diluted reactor samples containing the soluble components can also include GPC 27, two dimensional GPC, HPLC, temperature rising elution fractionation, various thermal, solvent gradient, and affinity chromatographies, MALDI-TOF (matrix associated laser desorption ionization-time of flight spectroscopy) and other types of polymer fractionation and batch measurements 31.

In the case of copolymerization, the resulting particles will often form self-organizing structures, such as, for example, micelles, aggregates, or emulsions. Copolymerization can also lead to core-shell structures. The present invention 10 will perform particle characterizing measurements such as listed above on all these different types of structures.

Molar mass M, and intrinsic viscosity are readily monitorable using the continuous, automatic dilution methods already patented by co-inventor herein, Reed, of which Automatic Continuous Online Monitoring of Polymerization Reactions (ACOMP) is an example. The present invention 10 provides that the extracted stream is divided into two or more streams 12 (or two streams or more streams withdrawn) and each resulting stream is separately treated so that at least one is diluted and conditioned to contain soluble components 13, whereas the other is diluted with a different solvent, or mixture of solvents, or not diluted at all, and contains a dispersion of particles 21. Each stream is then subjected to different characterizing measurements, e.g. particle characteristics are monitored in one stream while characteristics of soluble components are tested in another stream.

In the case of "oil in water" EPR, the characteristics of the soluble components will be determined in the first stream by dilution with organic solvents and/or mixed organic/aqueous solvents, or by adding in-line filters to remove water or aqueous solutions, and the usual flexible array of ACOMP detectors can be employed, such as any type of scattering detector, viscometer 15, differential refractometer 16, ultraviolet/visible spectrophotometer 17, fluorimeter 18, Fourier Transform Infra-Red spectrometer. The second stream will not be diluted at all or will be diluted by aqueous solution (which can contain any number of added agents, such as, for example, surfactants, and salts), which will conserve the particle characteristics of the polymer colloids, allowing this stream to be measured by particle characterizing instruments (e.g. DLS 22, HTDSLS 23 (currently for particle density determination, potentially expandable also to particle sizing), Electric Zone Sensing Method (often termed the 'Coulter Counter') 25, time of flight methods 26, and/or dielectric methods). In some instances characterizing measurements can be made on an extracted stream containing a dispersion of particles without any dilution step. Cases in which this may apply include, but are not limited to: EPR where a small concentration of monomer is used (e.g. 5% or less by mass); where a characterizing measurement, such as turbidity, is useful even if does not directly measure single particle properties as might be done if dilution were used; where a spectroscopic sample cell optical path length can be made very small (e.g. 0.1 mm for a UV/visible spectrophotometer flow cell), so that usable spectroscopic signals can be obtained without dilution; or various light back-scattering techniques on concentrated solutions, such as diffusing wave spectroscopy.

In the case of "water in oil" EPR, or inverse emulsions, the polymer/monomer characteristics will be determined by dilution with aqueous solution (which can contain any number of added agents, such as, for example, surfactants, salts), or by adding in-line filters to remove oil, and the usual flexible array of ACOMP detectors can be employed such as any type of scattering detector, viscometer 15, differential refractometer 16, ultraviolet/visible spectrophotometer 17, fluorimeter 18, Fourier Transform Infra-Red spectrometer. The second stream will be diluted by organic solvents and/or mixed organic/aqueous solvents, if diluted at all, which will conserve the particle characteristics of the polymer colloids, allowing this dilute stream to be measured by particle characterizing instruments (e.g. DLS 22, HTDSLS 23 (currently for particle density determination, potentially expandable also to particle sizing), Electric Zone Sensing Method (often termed the 'Coulter Counter') 25, time of flight methods 26, and/or dielectric methods). While not intended to be limiting, it is noted that the polymer characterizing dilution is usually much less (on the order of 10× to 1000×) than the particle characterizing dilution (on the order of $10^4 \times$ and higher).

It is noted that the extracted streams can be passed through multiple characterizing systems. For example, the continuous flow of the colloid stream, whether diluted or not, may pass through a series of continuous detectors (e.g. DLS 22 and HTDSLS 23), and upon emerging, portions of this stream can be periodically (and automatically, if desired) injected into a fractionating (e.g. hydrodynamic capillary fractionation) or "batch" measuring unit (e.g. an Electrical Zone Sensing device) 31. The continuous flow of the colloid stream can also be injected into a fractionating measurement system without passing through continuous measurement detectors. In the case of interrupted measurements, periodic samples may also be taken from the stream for those types of particle characterization devices that are not flow-cell equipped.

Likewise, the soluble-component characterizing stream can first pass through continuous detectors (such as MALS 14, viscometer 15, RI 16, and UV/visible spectrophotometer 17) and then be periodically (and automatically, if desired) injected into a GPC 27 or other fractionation system, as is currently sometimes done in relation to known automatic continuous dilution methods (e.g. U.S. Pat. No. 6,653,150). The continuous flow of the soluble-component stream can be periodically injected into a GPC 27 or other fractionation system without first passing through continuous measurement detectors. "Periodic" in this context may mean at regular or irregular intervals, including intermittent measurements not equally spaced.

ACOMP is a very new method in which only a limited number of people are skilled in the art (about 12 people worldwide). Those working with emulsions usually focus on one aspect or on another aspect of the emulsion polymer characteristics (e.g. on conversion or on particle sizing and particle density). The different methods used to measure the various characteristics such as particle sizes, conversion, and polymer characteristics, are disjoint, distinct and separate, requiring different equipment and analysis arrangements, e.g. a DLS system for sizing, a GPC system for polymer mass determination, and a drying/weighing system (or perhaps NMR or other device) for determining polymer concentration (and hence monomer conversion), and/or a GPC system for both mass and conversion measurements. The present invention unifies the analytical procedures that heretofore have been carried out in disjoint, distinct and separate ways.

Substantiating Data

Figure 7:
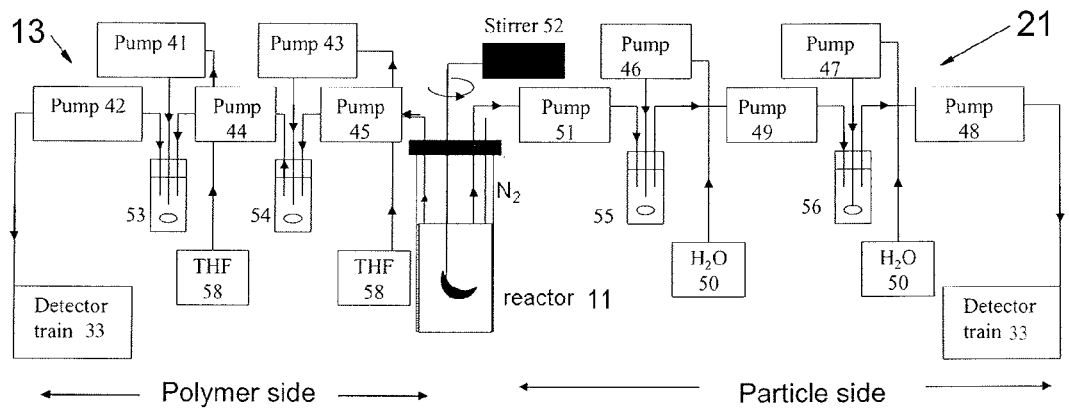
FIG. 7 is a schematic flow chart of the preferred embodiment of the apparatus of the present invention prior to reaching the detector train.

Experimental Demonstration of Simultaneous Monitoring of Polymer and Particle Characteristics During Emulsion Polymerization As a first example of the uses of the present invention 10 an embodiment of the device was made and a method developed for a specific application: the free radical polymerization of methyl methacrylate, MMA, (and, separately, butyl acrylate, BA) in surfactant free emulsion. FIG. 7 is a typical setup for the extraction and dilution/conditioning of the reactor content/liquid before reaching the characterizing measurement equipment, also referred to as the "detector train" 33.

Typical flow rates in the reactions presented below were: Extraction (Q-pumps 1 and 2) 45, 51 at 0.1 to 0.2 mL/minute; Dilution factors were from 100 to 500 on the polymer and particle sides. None of these flow rates or dilution factors are to be construed as limiting. It was straightforward to take into account the different delay times between extraction and measurement in the polymer and particle sides, which were typically a couple hundred seconds.

Polymerization reactions were performed in a 500 ml reactor purged continuously with $N_2$. The initiator, potassium persulfate ($K_2S_2O_8$) and the monomers, methyl methacrylate (MMA) and butyl acrylate (BA) were used as received from Acros Organics. A Ross homogenizer at 1800 rpm was used a stirrer 52 to mix the reactor contents throughout the reaction.

Two streams were extracted simultaneously from the reactor. An organic solvent THF 58 was chosen as liquid to solubilize soluble components and to further dilute (in two stages) the first stream withdrawn from reactor for studying soluble component (polymer/monomer) characteristics. $H_2O$ 50 was the liquid to disperse colloid components and to dilute the other stream (in two stages) for monitoring particle number and size distributions. Low pressure mixing chambers (LPMC 1-4) 53,54,55,56 were used as reservoirs for dilution. Various pumps were involved in the dilution/conditioning of the reactor content withdrawn: For the polymer side, an Agilent1000 HPLC pump 43 was used in a first dilution/conditioning step (LPMC2 54) to dilute with THF the first stream withdrawn from reactor with Q-pump1 51; the diluted emulsion was pumped with a HPLC Knauer pump1 44 into a second LPMC (LPMC1 53), where a subsequent dilution with THF wad made by the use of a HPLC Shimadzu ADvp1 41 which brought THF at a 2 ml/min flow rate. Finally, another HPLC Shimadzu ADvp pump2 42 was used to pump the diluted emulsion through detector train at 1 mL/min on polymer side. Similarly, in the case of the particle side, the second stream withdrawn from the reactor (Q-pump2 45) was diluted with $H_2O$, bought into LPMC3 55 by a peristaltic pump 46 at ~2 ml/min. In a second dilution/conditioning step, the diluted emulsion is pumped with a HPLC Knauer pump2 49 into LPMC4 56, where it is subsequently diluted with $H_2O$, brought by a HPLC Waters pump 47 at ~2 ml/min. From here, the diluted emulsion is pumped with a HPLC Eldex pump 48 at 2 mL/min into the detectors on the particle side. As it exists the last detector on both polymer and particle side, respectively, the diluted emulsion goes to waste 20. Capillary tube of different length and size, from small diameter tube 70, to medium diameter tube 71, or large diameter tube 72 could be used as pump lines and to flow the liquid between the detectors.

Different detectors were used depending on the polymer/particle features monitored. Due to the complexity of the system, three computers PC 60 were used to collect the signals from the various detectors involved in the monitoring of each polymerization reaction performed. Commercial or specially made software were used in data analysis.

Figure 4:
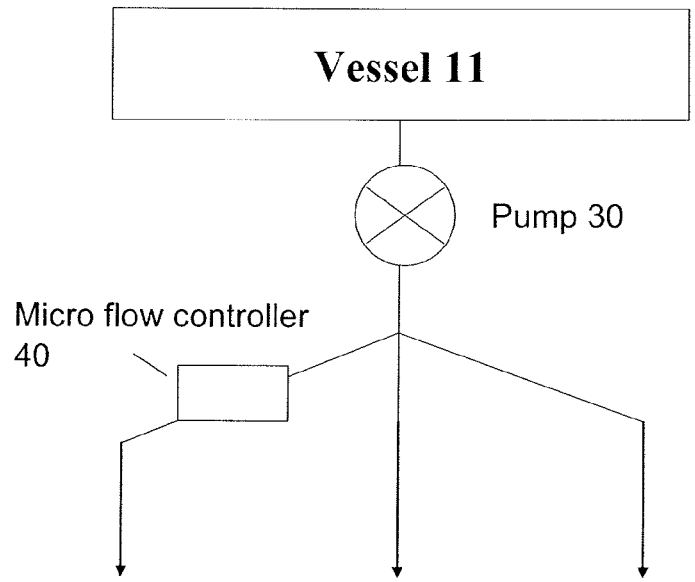
FIG. 4 is an alternate preferred embodiment of the present invention.
Figure 5:
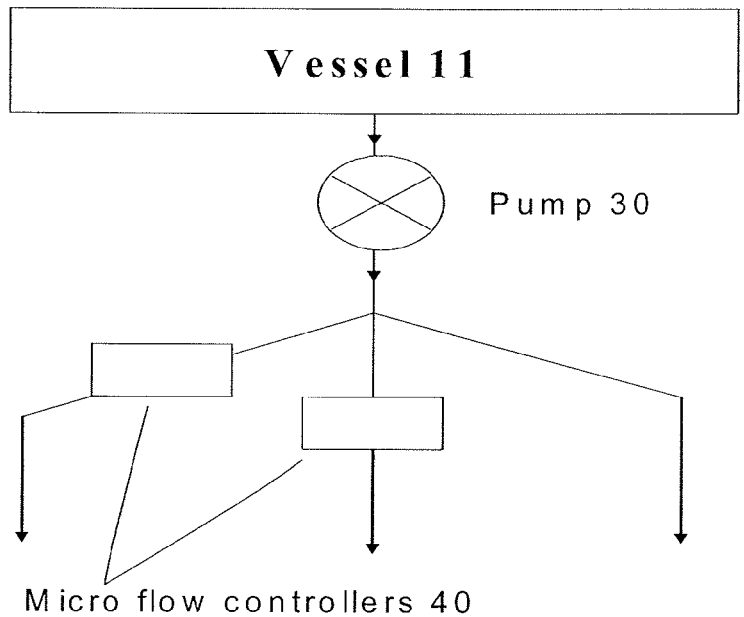
FIG. 5 is an alternate preferred embodiment of the present invention.
Figure 6:
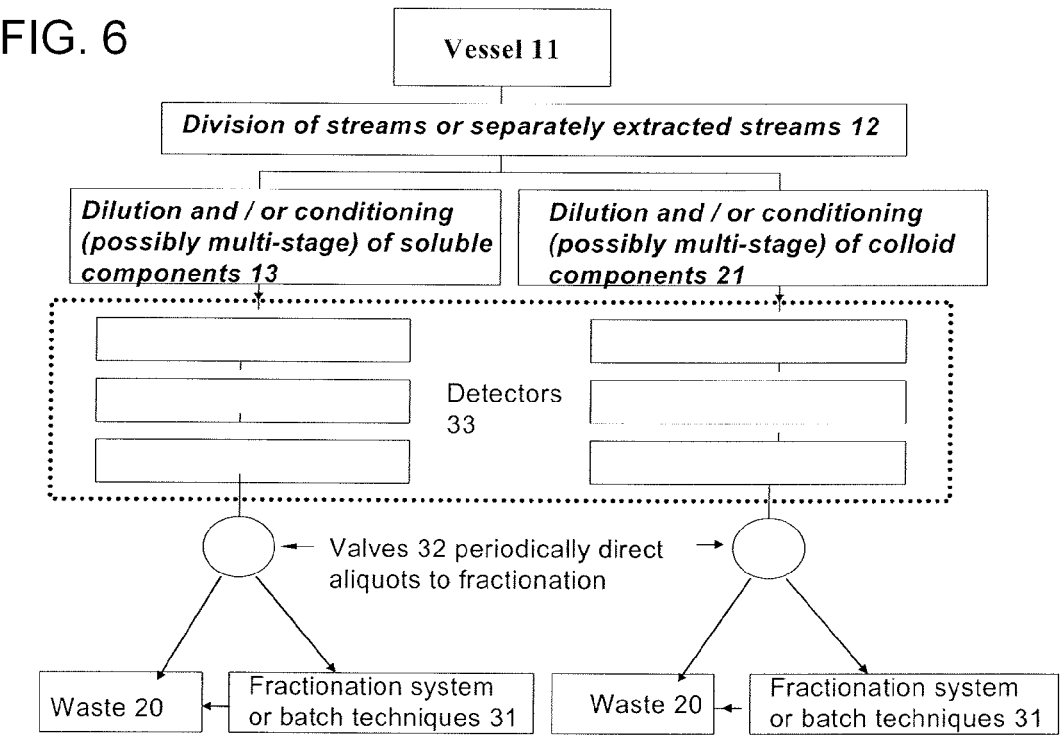
FIG. 6 is a schematic flow chart of the preferred embodiment of the method of the present invention.

FIG. 4 shows a stream from vessel 11 split into three tributaries or capillaries, including a first tributary or capillary, a second tributary or capillary, and a third tributary or capillary, with a micro flow controller 40 controlling one tributary or capillary.

Polymer side (Soluble Component Stream): A 2 μm inline frit was included between the pump 30 and the detector train: A custom built capillary viscometer 15, a refractive index, or RI detector 16 (410 Waters), MALS 14 (BIMwA, Brookhaven) and UV/V is (SPD-10AVvp, Shimadzu) detectors 17. The reactor emulsion diluted with THF 58 was passed through detectors 33 at 1 ml/min during the reaction.

Particle side (Particle Stream): The emulsion diluted with $H_2O$ 50 was passed at 2 ml/min through a particle size detector (Mastersizer2000, Malvern Instruments). Measurements were made continuously on the reactor emulsion diluted with $H_2O$ 50 and passed at 2 ml/min through the cell of the detector during the polymerization reaction. The Mastersizer2000 analyzes scattered light at about fifty different angles, and uses the Mie scattering theory to evaluate particle sizes and to approximate size distributions. It uses British Standards document BS2955:1993 for defining the different averages and characteristics of the particle population (e.g. D(v,0.5) (mass median diameter), D(v,0.1), and D(v,0.9) are the sizes (in μm) below which 50% 10%, and 90% respectively, of the sample lies; D[4,3] is the volume mean diameter, D[3,2] is the surface area mean diameter), specific surface area is surface area per mass.

Results from several emulsion polymerization reactions of methyl methacrylate (MMA) and butyl acrylate (BA) monitored are shown in table 1. The reactions conditions were varied, and show strength and versatility of the present invention for monitoring a broad range of polymerization reactions in emulsion, including from surfactant-free reactions to reactions with surfactant (SDS sodium dodecyl sulfate) added, and from dilute regime (~4%) to high yield reactions (~35%).

The present invention 10 allows the reactions in the vessel 11 to be characterized in terms of monomer conversion, mass and reduced viscosity of the polymer, together with the size distribution of the latex particles produced. A video camera was used to record the visual evolution of the reactor content during the polymerization, and thus to offer a means to correlate macroscopic parameters with microscopic ones. If copolymerization is carried out in emulsions, the method of Alb, Reed et al. (Macromolecules 2006) monitors the composition drift and average composition distribution during the reaction, and yields a complete characterization of the final product in terms of average mass, composition, and intrinsic viscosity distributions.

Traditional multi-detector SEC and DLS 22 (Brookhaven Instruments Corp. 90Plus Particle Sizer) were used to cross-check the results of the present invention, by making discrete measurements on aliquots manually withdrawn from the reactor during the polymerization reaction.

1. Dilute Regime. Emulsion Polymerization of BA and MMA

TABLE 1

Emulsion polymerization of BA and MMA (dilute regime) at low concentration. In the case of reaction #1 no surfactant was used, whereas in the case of reaction #2 surfactant sodium dodecyl sulfate (SDS) was used.

| Reaction # | $C_{M,r}$ (M) | [M]/ [K$_2$S$_2$O$_4$] | $C_{SDS}$ (M) | $M_{w@f=1}$ (g/mole) | $\eta_w$ (cm$^3$/g) | $D_{h,DLS}$* (nm) | $D[4,3]_{Mie}$* (nm) |
|---|---|---|---|---|---|---|---|
| 1 BA | 0.270 | 170 | — | $1.2 \times 10^6$ | 400 | 254 | 410 |
| 2 MMA | 0.458 | 299 | $8.075 \times 10^{-3}$ | $2.5 \times 10^6$ | 400 | 54 | 109 |

*values at final conversion

Experiment #1 is a case of surfactant-free emulsion polymerization of butyl acrylate BA. The very low BA solubility affects the initiation step of the reaction mechanism and hence, reaction kinetics. The PBA (polyBA—poly(butyl acrylate)) end products have higher molecular weight and viscosity than PMMA (polyMMA—poly(methyl methacrylate)).

Particle size measurements were made on the emulsion samples automatically and continuously withdrawn from the reactor 11 during the polymerization reaction using the extraction/dilution scheme shown in FIG. 7. The dilution in two stages of approximately 440× was made with H$_2$O 50. The characterization measurement analysis produces a volume distribution (the volume proportion in each size class of the total volume of the particles) which is converted to a specific type of distribution (e.g. number, surface or length distributions).

Results for Reaction #1 (BA. No Surfactant)

Figure 8:
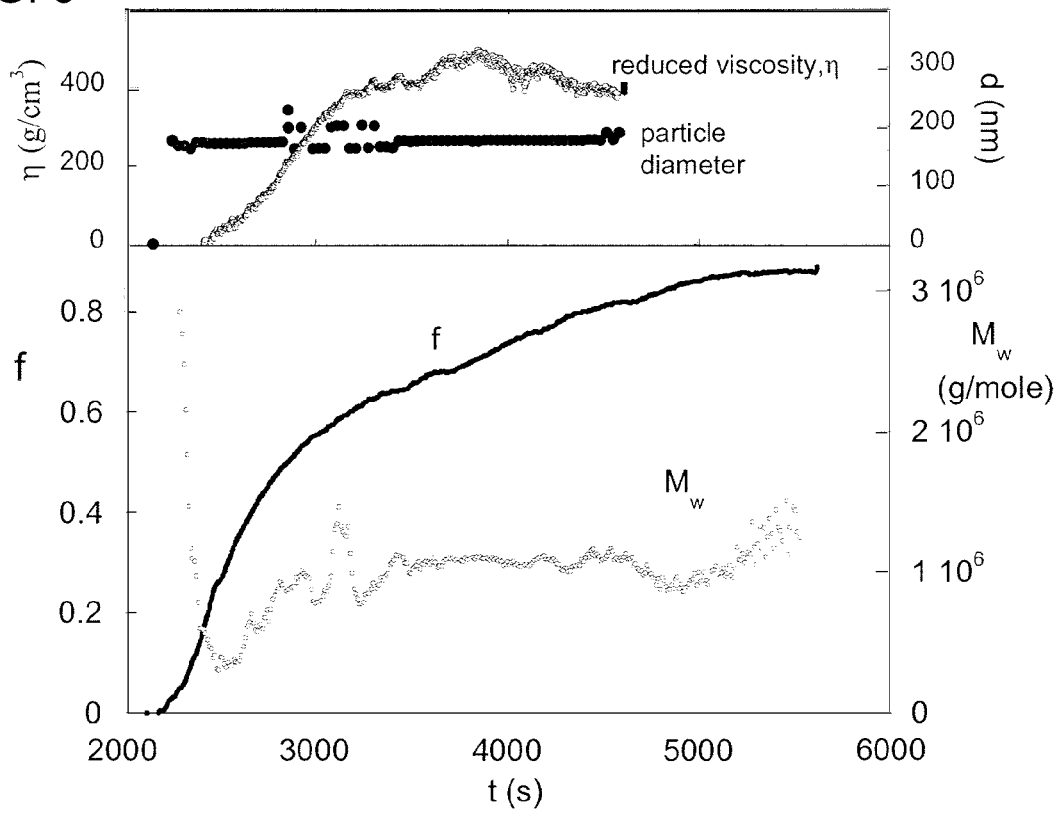
FIG. 8 shows conversion and $M_w$ vs. time (below) from the polymer side. Above is reduced viscosity (from polymer side) and particle size from the particle side.

FIG. 8 shows fractional monomer conversion and weight average polymer mass, $M_s$, computed from raw data for experiment #1 and shown as functions of time. The upper part of the figure shows reduced viscosity and particle size evolution, where particle size evolution was measured on the particle side and corresponds to the colloid particles in which polymers are being created. The particle diameter d(0.5) remains remarkably constant throughout the reaction, around 180 nm.

Figure 9:
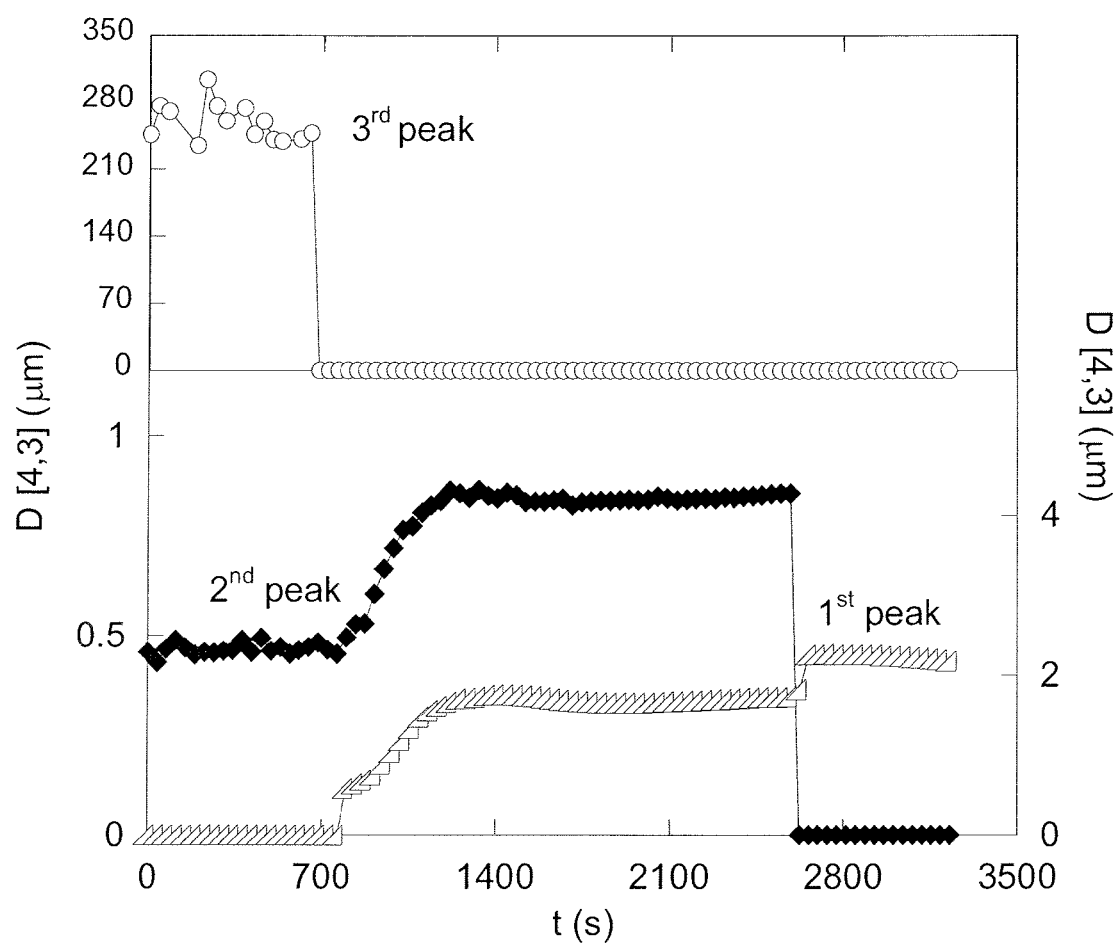
FIG. 9 shows D[4,3] vs. time for Reaction #1.

The size distribution of the particle side calculated from automatic Malvern Mastersizer measurements taken each 35 s is multimodal, big particles being present for different periods of time during the reaction. FIG. 9 shows the trend in the evolution of three types of modes observed in the particle size evolution, e.g. D[4,3]: the biggest particles (3$^{rd}$ peak) last for ~10 min, at which moment the small particles are produced (1$^{st}$ peak). There is an intermediate mode which exists until nearly the end of reaction. The smallest particles (D[4,3]~340 nm), which represent the polymer particles show a slight increase in size as the reaction proceeds, and the bigger particles disappear, marking the consumption of the monomer and the hence the disappearance of the monomer droplets.

Figure 10:
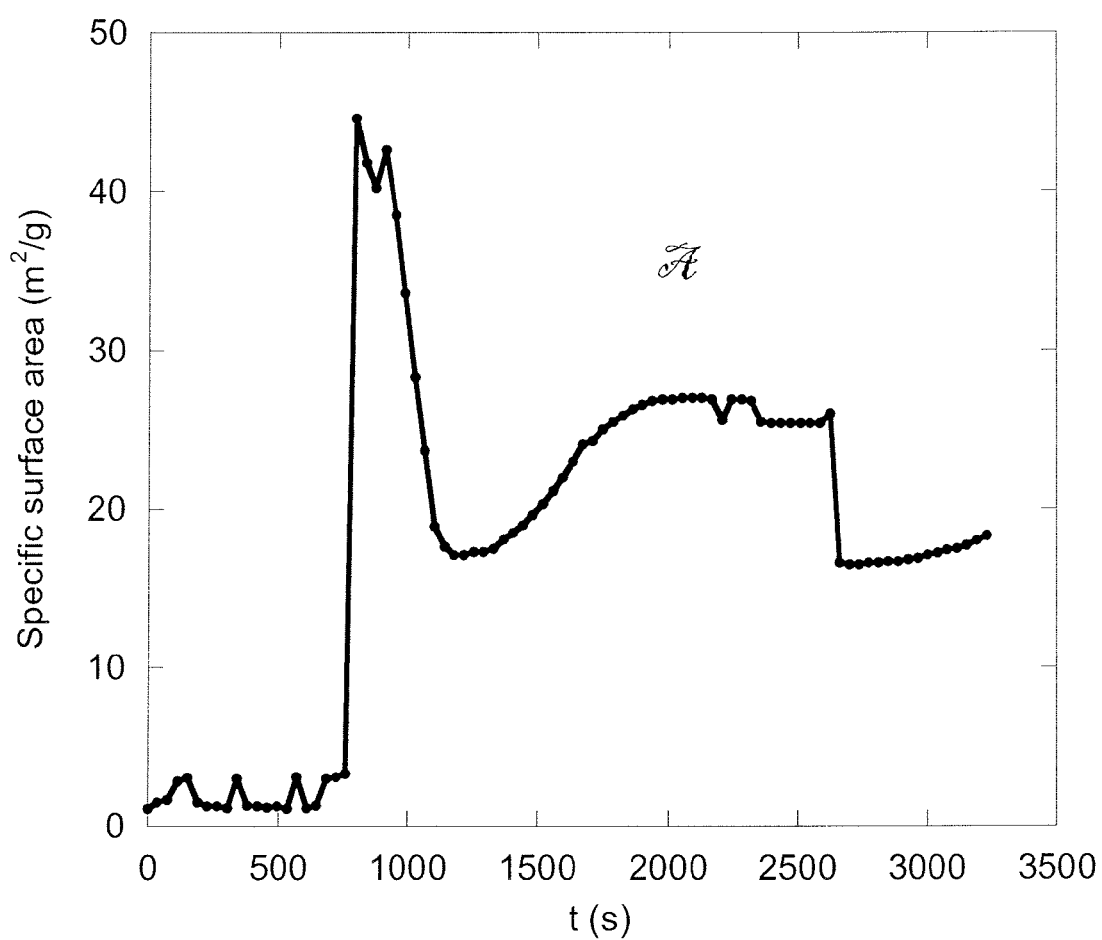
FIG. 10 shows specific surface area vs. time for Reaction #1.

In FIG. 10 the increase of the specific surface area $\mathscr{A}$ follows the particle growth. It is seen that there is a very short nucleation time, ~12 min, until the nucleated polymer particles are initially produced.

Results for Reaction #2 (MMA with Surfactant)

In Reaction #2, the MMA polymerization reaction was done in the presence of surfactant. The addition of surfactant improved the emulsion stability.

Figure 11:
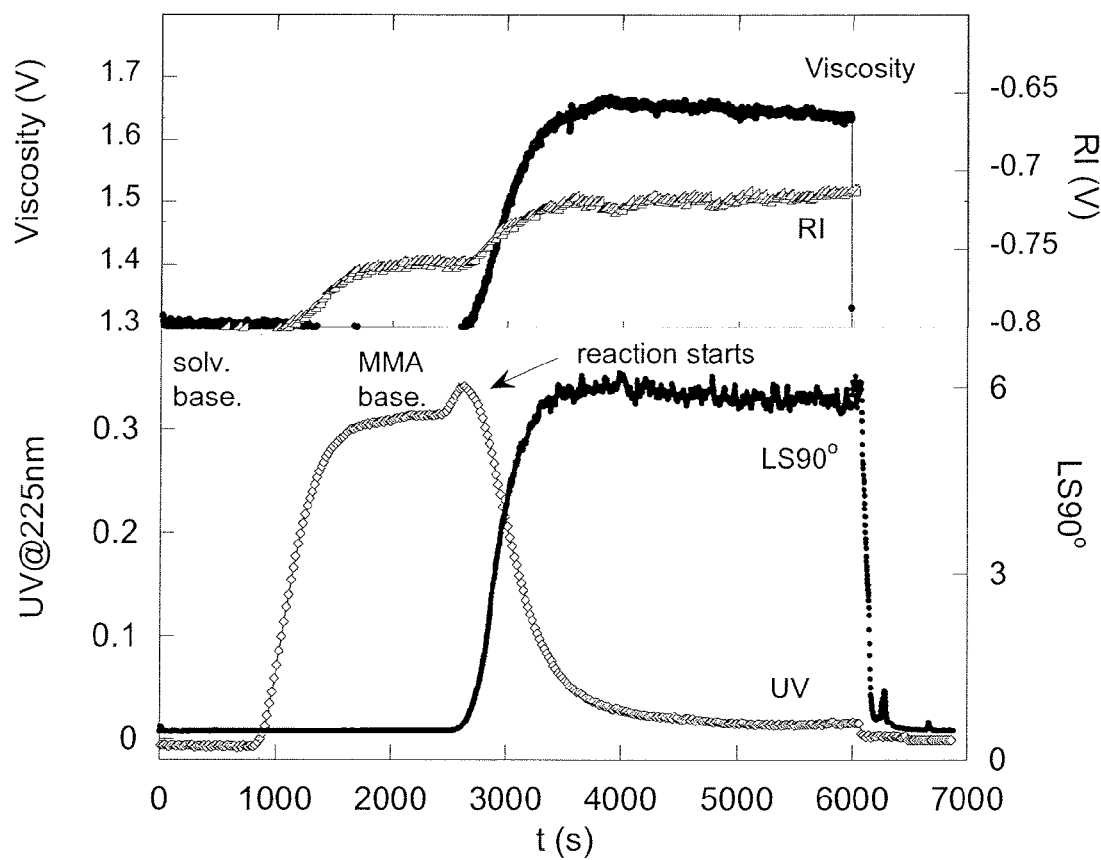
FIG. 11 shows raw LS90°, viscosity and UV@225 nm for Reaction #2 vs. time.

FIG. 11 shows raw LS90°, viscosity and UV@225 nm for experiment #2.

Figure 12:
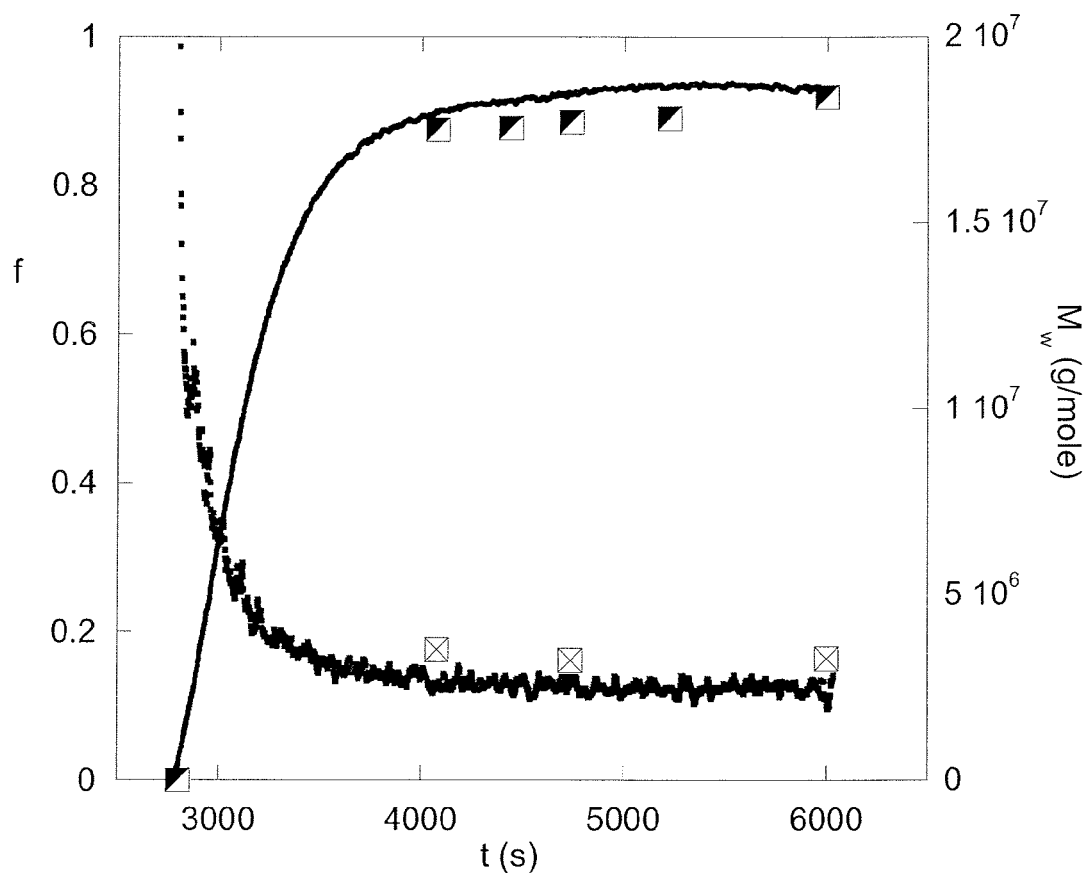
FIG. 12 shows the evolution of the monomer conversion and the polymer mass, Mw during the polymerization Reaction #2.

The evolution of the monomer conversion and the polymer mass, $M_w$ during the polymerization reaction are shown in FIG. 12, computed from raw data above in FIG. 11. The discrete squares are SEC results from discrete measurements on manually withdrawn aliquots taken during reaction. These discrete manual measurements are in agreement with ACOMP values obtained through the present invention 10.

Figure 13:
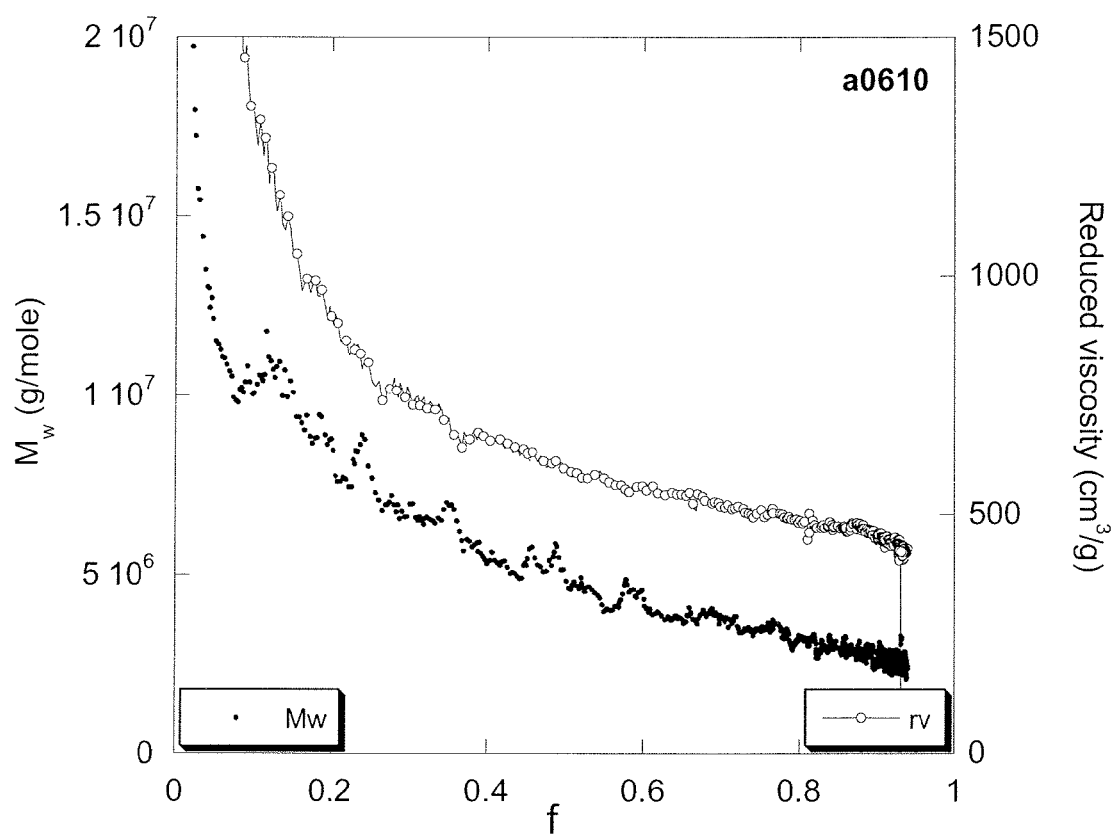
FIG. 13 shows reduced viscosity $\eta$ and molecular mass Mw vs. monomer conversion for Reaction #2.

Reduced viscosity $\eta$ and molecular mass $M_w$ are shown vs. monomer conversion in FIG. 13. Higher $M_w$ and $\eta$ are observed in the case of reactions with surfactant added.

Size Measurements for Reaction #2.

Figure 14:
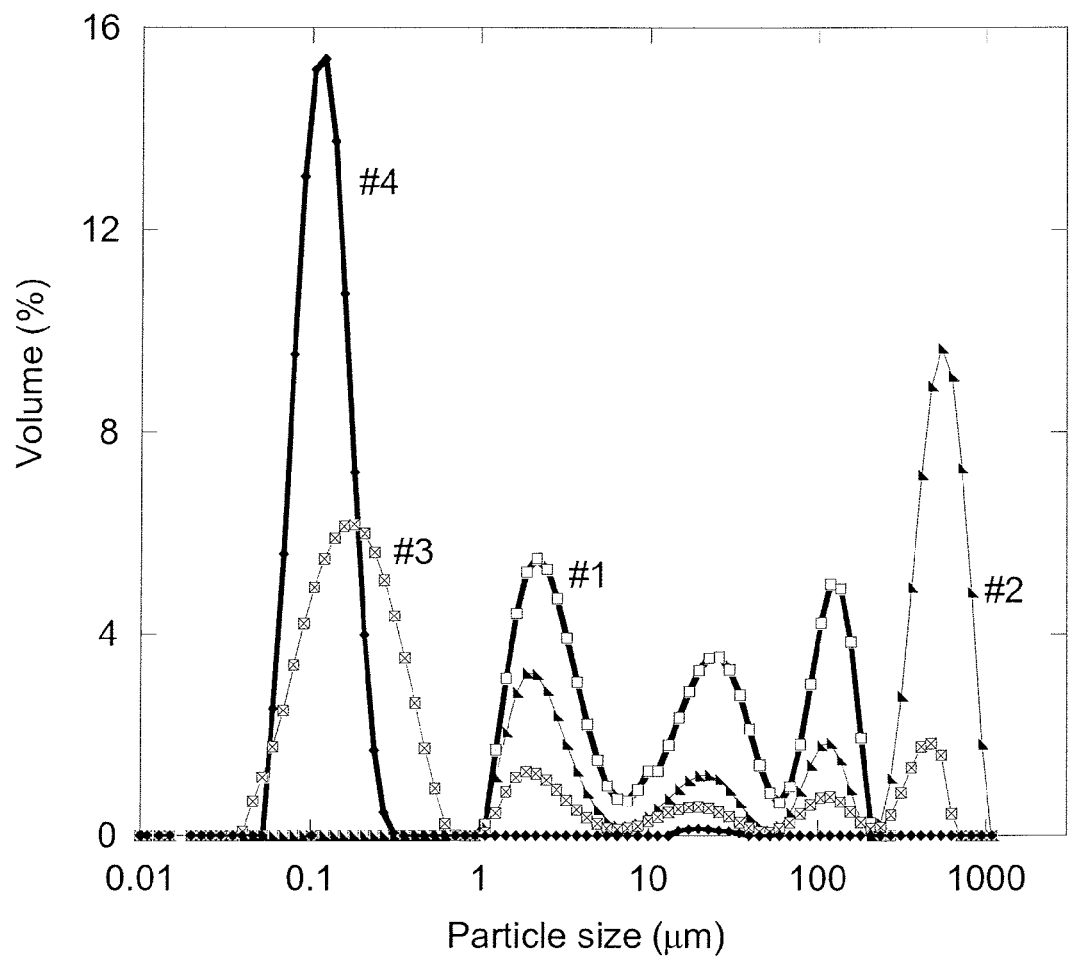
FIG. 14 shows a few selected particle size distributions from the many distributions measured online during the MMA polymerization of Reaction #2.

FIG. 14 shows a few selected particle size distributions from the many distributions measured online during the MMA polymerization of Reaction #2. The tendency is for the large diameter modes to decrease during the reaction and for the low diameter mode to increase. In FIG. 14 #1, #2, #3, and #4 refer to selected distributions, as the reaction proceeds, from the many distributions collected automatically throughout the reaction.

Figure 15:
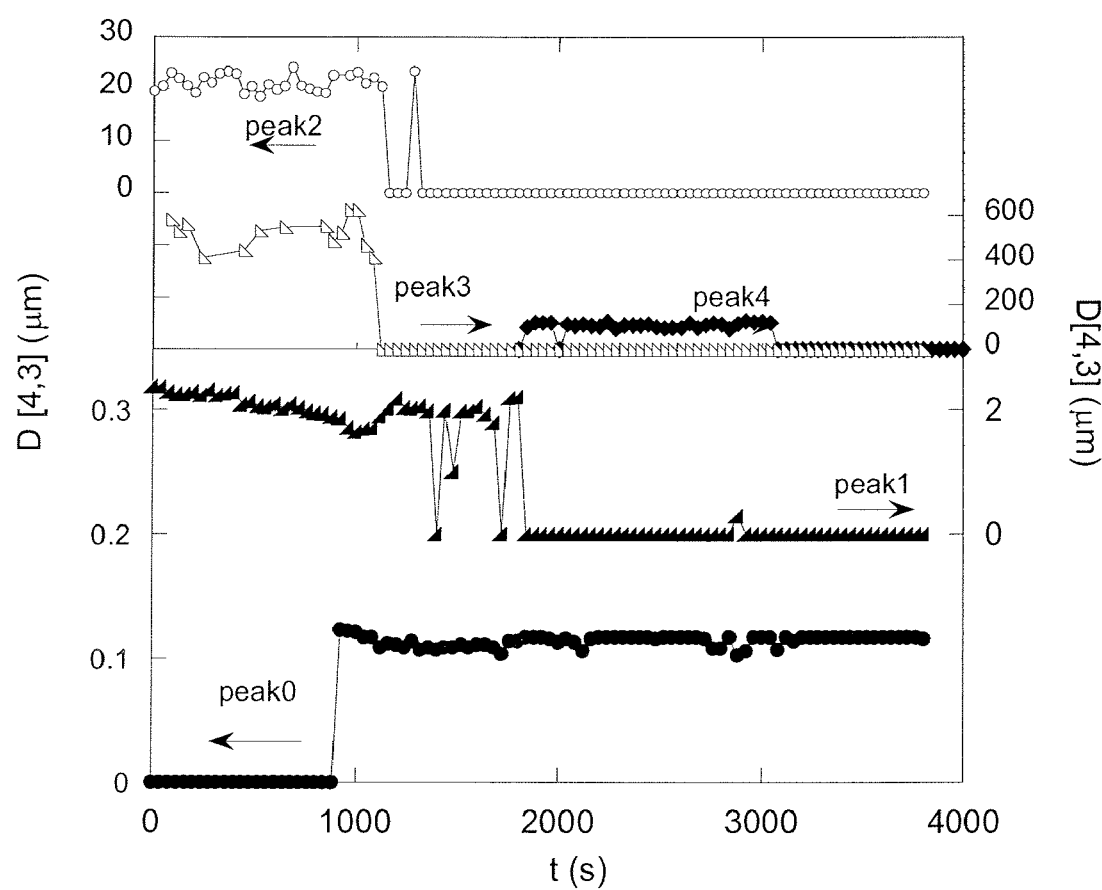
FIG. 15 shows the evolution of the volume weighted mean diameter, D[4,3] for all the modes in the particle size distribution taken from the many distributions measured during Reaction #2.

FIG. 15 shows the evolution of the volume weighted mean diameter, D[4,3] for all the modes in the particle size distribution taken from the many distributions measured during Reaction #2.

A very short time for the growth of particles in which polymer chains are created is suggested by the rapid appearance of the smallest mode (peak 0 at around 0.1 µm), and the decrease in the size averages of the other, larger modes. The polymer peak shown in FIG. 15 (~0.1 µm) appears at 900 s, whereas the peak corresponding monomer droplets (0.1 µm) disappears at t=1200 s. The data in Table 2 substantiates these findings.

2. High Concentration—BA Emulsion Polymerization Reactions, with and without SDS

TABLE 2

Reaction parameters for high concentration BA emulsion polymerization reactions with and without surfactant.

| React. # | [BA] | [I] = [K$_2$S$_2$O$_4$] | [BA]/[I] | [SDS] | $D_{h,DLS}$* (nm) | $D[4,3]_{Mie}$* (nm) | $M_{w,q=0,f=1}$* (g/mole) | $M_{w,90,f=1}$* (g/mole) | $\eta_w$* (cm$^3$/g) |
|---|---|---|---|---|---|---|---|---|---|
| 3 | 1.11 | 5.586 × 10$^{-3}$ | 199 | — | 517 | 550 | 5.00 × 10$^6$ | 2.30 × 10$^6$ | 760 |
| 4 | 2.53 | 8.319 × 10$^{-3}$ | 304 | 6.549 × 10$^{-3}$ | 80 | 112 | 1.45 × 10$^7$ | 4.00 × 10$^6$ | 1250 |

*values at final conversion

Figure 16:
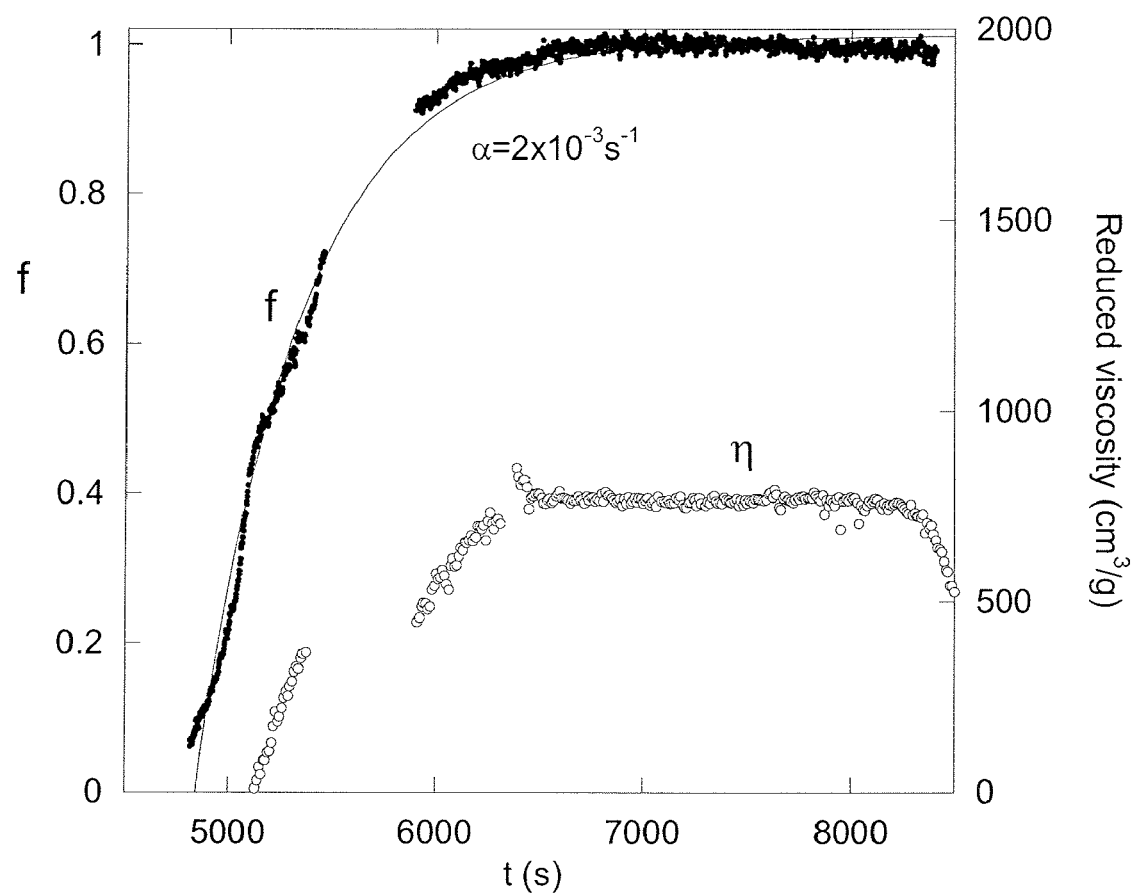
FIG. 16 shows conversion f, and reduced viscosity, $\eta_r$ vs. time for Reaction #3.
Figure 17:
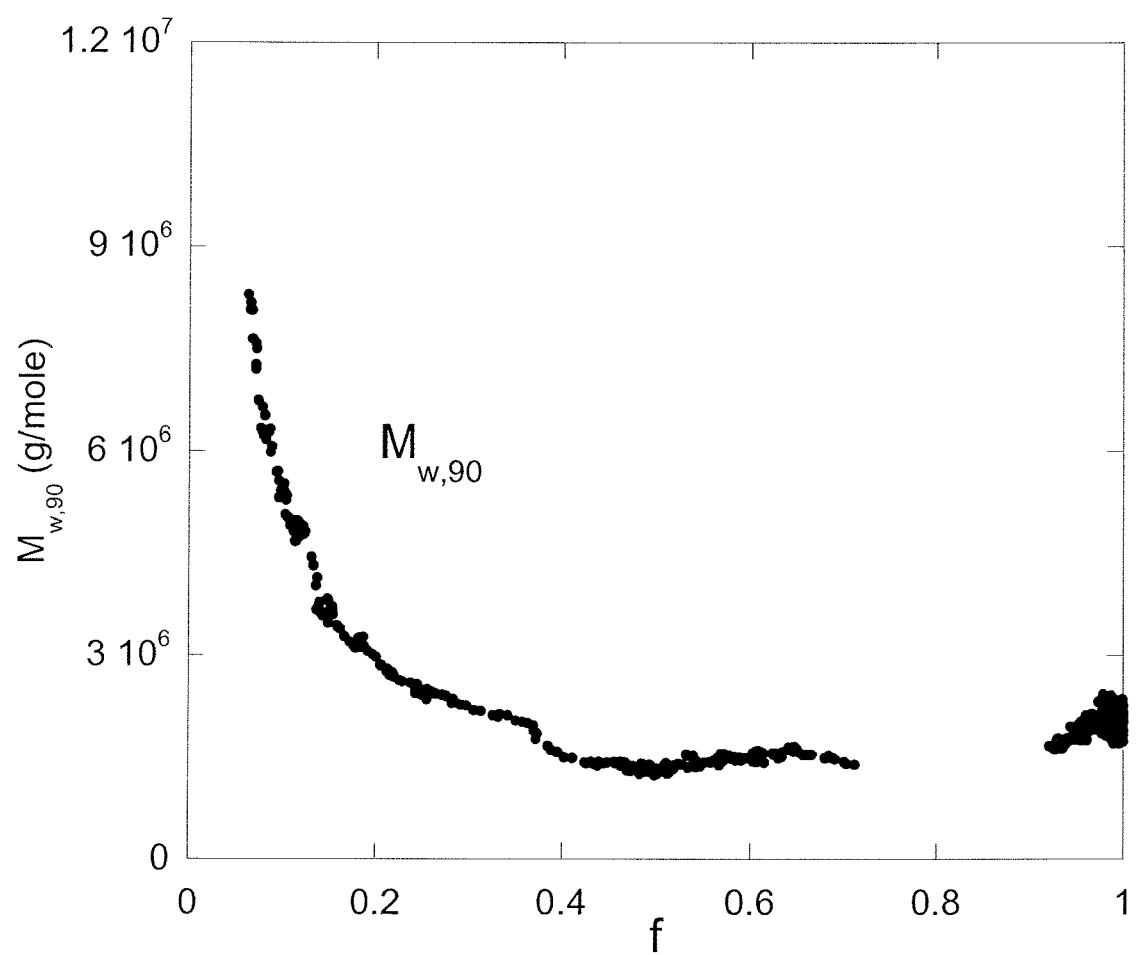
FIG. 17 shows weight-average molecular mass, $M_w$ vs. conversion for Reaction #3.

Results for Reaction #3. Surfactant-Free Emulsion Polymerization of BA at 70° C., Polymer Characterization FIG. 16 shows conversion, f, and reduced viscosity, $\eta_r$ vs. t. FIG. 17 shows weight-average molecular mass, $M_w$.

Figure 18:
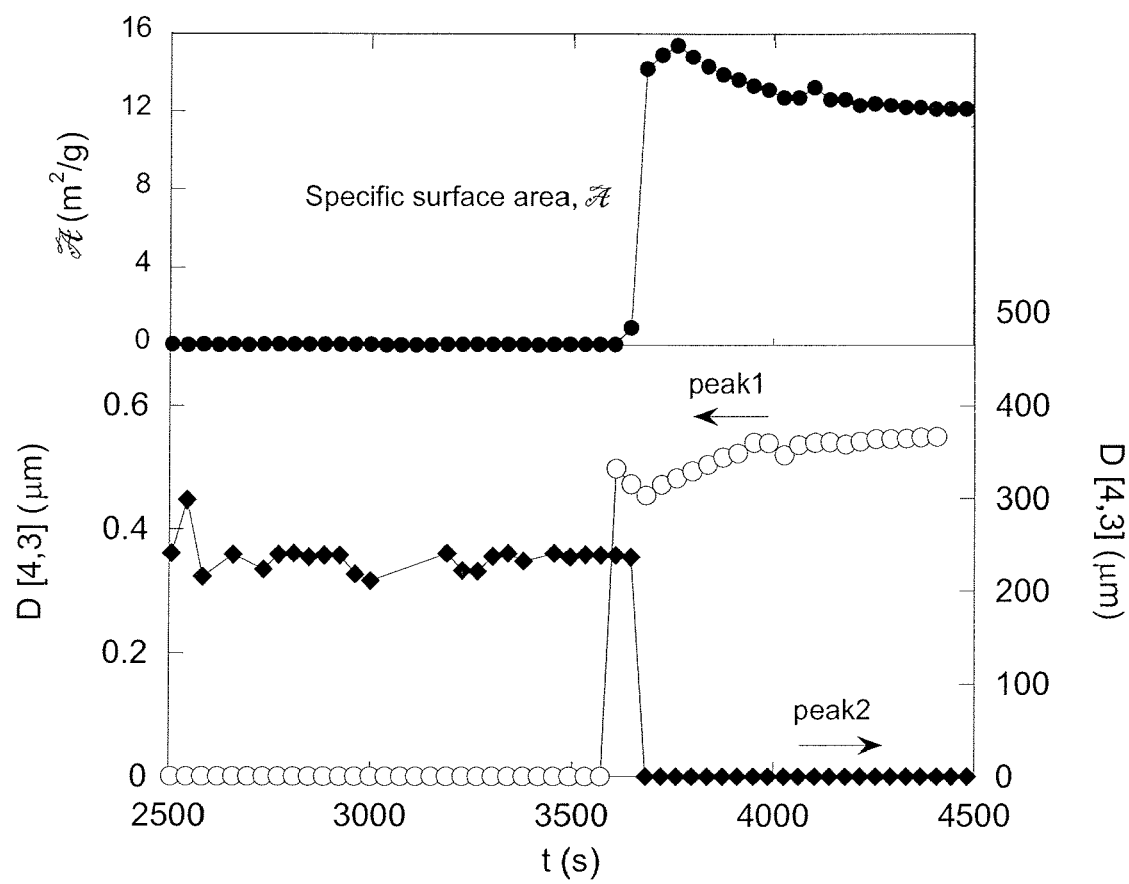
FIG. 18 shows the evolution of D[4,3] (below) and of the specific surface area $\mathscr{A}$(above) from the particle side as Reaction #3 proceeds.

The evolution of particle size for Reaction #3 was monitored by measurements on the particle side made at 38 s intervals. Two modes are observed in all the moments of the size distribution, shown here in FIG. 18 is D[4,3]: one for large particle size, D[4,3]~240 μm, and a second one for smaller particle size, D[4,3]~0.54 μm. The first mode (peak 2) corresponds to monomer droplets disappearance and the second mode (peak 1) corresponds to formation of particles containing polymer chains. The upper part of FIG. 18 shows the evolution of the specific surface area $\mathscr{S}$ as the reaction proceeds. The decreasing trend indicates a tendency toward coagulation between the polymer particles.

Figure 19:
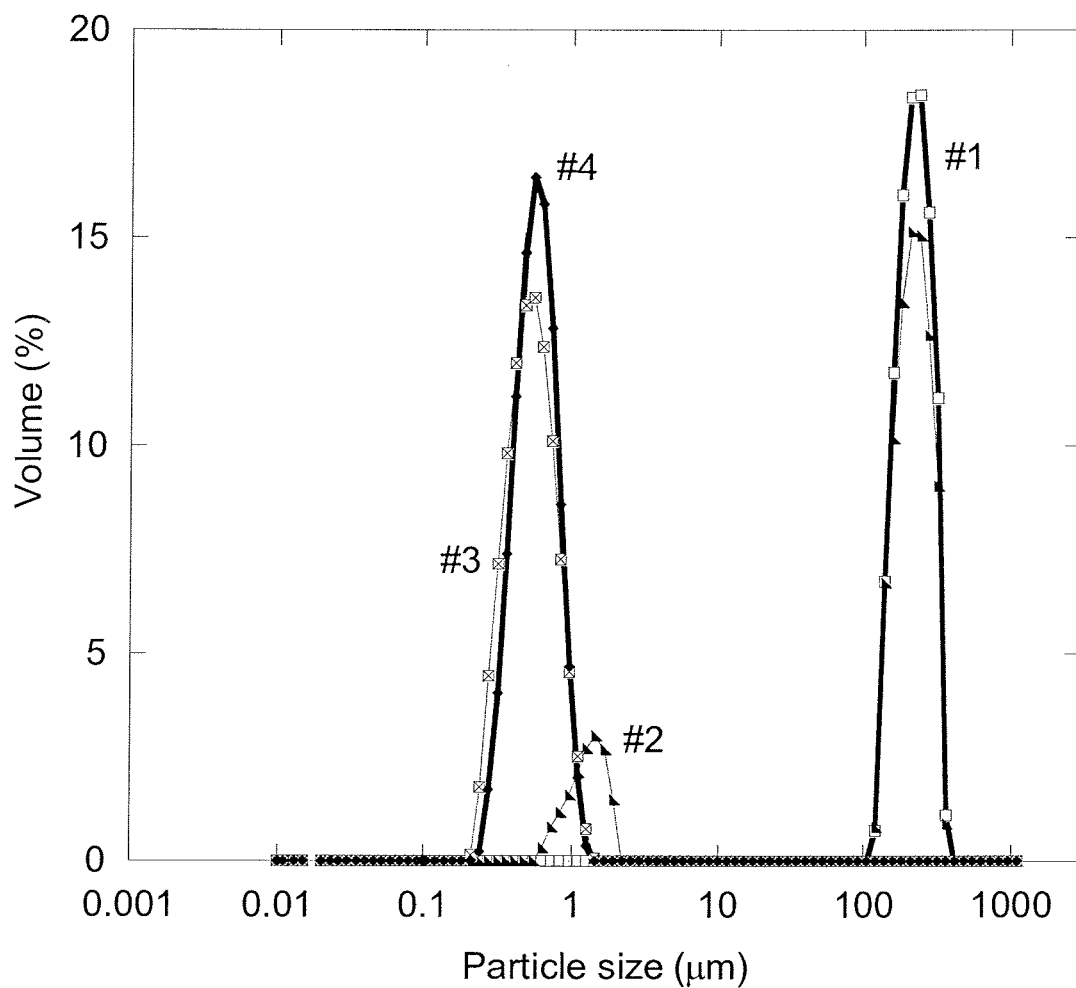
FIG. 19 shows a few selected particle size distributions from the many measured during Reaction #3.

FIG. 19 shows a few selected particle size distributions from the many measured during Experiment #3.

Results for Reaction #4; Emulsion Polymerization of BA in the Presence of Surfactant (SDS) at 70° C.

Obtaining high polymer yield in an emulsion polymerization makes industrial production more efficient; however, going to high monomer concentration regime in emulsion reactions brings some disadvantages. Deviations from ideal kinetics, coagulation/aggregation, and exothermicity effects are among the negative aspects of working with a high monomer concentration in reactor and thus are problems overcome by the present invention. Online monitoring of both particle and polymer characteristics with the method and apparatus of the present invention 10 allows one not only to study reaction kinetics, but also to observe any deviations, and, potentially, to intervene and hence save valuable raw materials, energy, non-renewable resources, and plant and personnel time.

Polymer Characterization for Reaction #4.

Figure 20:
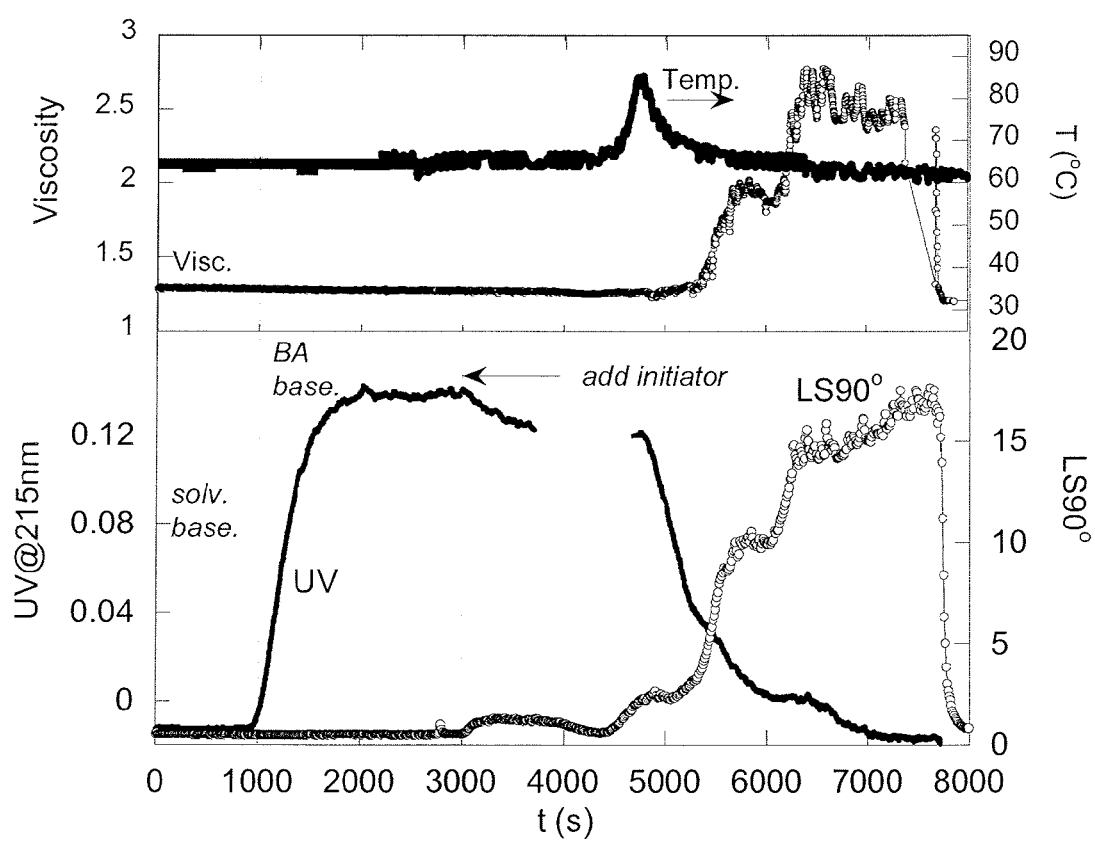
FIG. 20 shows raw LS90°, viscosity, temperature, and UV@225 nm voltages vs. time for Reaction #4.

FIG. 20 shows raw LS90', viscosity, temperature, and UV@225 nm voltages are shown for Reaction #4. A pronounced temperature spike is observed at the outset of the reaction, arising from the exothermicity of the reaction, which is more pronounced due to the high reactant concentration.

Higher values of $M_w$ and $\eta_r$ are obtained in Reaction #4 compared to the results from the same reaction done in the absence of surfactant in Reaction #3.

Demonstration of the Present Invention when the Particle Measurements are Made on an Undiluted Stream after Extraction from the Reactor:

Reaction #5: Surfactant-Free Emulsion Polymerization of Methyl Methacrylate (MMA)

Methyl methacrylate (MMA) was chosen and its polymerization in emulsion was monitored with the simultaneous detection method of the present invention without diluting the extracted stream used for particle characterization.

ACOMP Conditions for Reaction #5.

Once prepared, the monomer emulsion was agitated 5 min with a Ross homogenizer to help the stability of the emulsion components.

The LPMC, whose content (smaller volume than in the previous trials, to decrease the residence time) was heated to 50° C. in order to help the mixing of the emulsion with THF 58. This change had beneficial effects on the pump performance (Shimadzu) 41, 42 and hence on the quality of data.

The conditions for Reaction #5 were as follows: the solvent used in reactor was H$_2$O 50, the diluent in LPMC was THF 58, the monomer was methyl methacrylate MMA, the initiator was K$_2$S$_2$O$_8$. The mass concentration in the reactor and detector were as follows: $C_{MMA,reactor}$=46.8/mg/ml (0.4674M), $C_{MMA,detectors}$=1.95/mg/ml, $C_{H2O,detectors}$=39.583/mg/ml.

Figure 21:
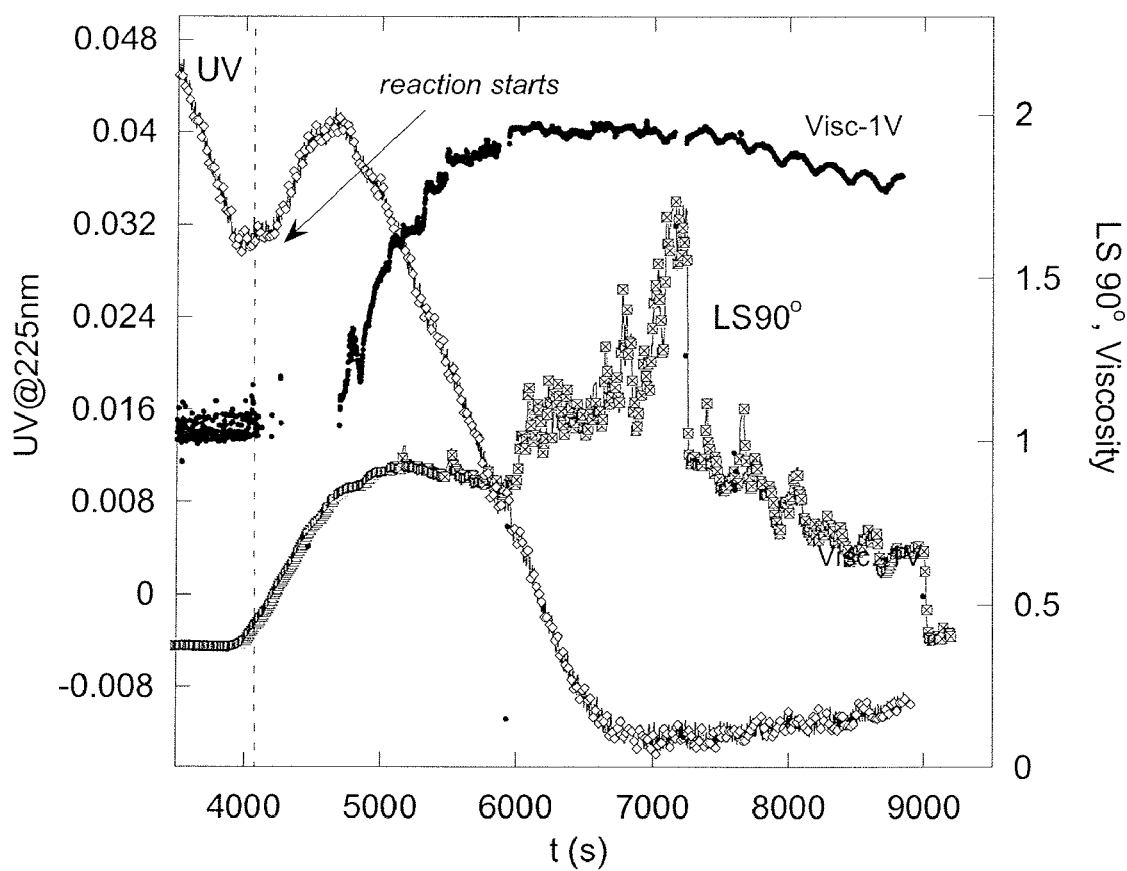
FIG. 21 shows raw LS, Viscosity and UV@225 nm voltages vs. time for Reaction #5.

Raw LS, Viscosity and UV@225 nm voltages are shown in FIG. 21 for the stream that was withdrawn and diluted with THF 58 in order to monitor polymer/monomer properties as they evolved. The reaction began at approximately 4000 s. The build-up of viscosity and light scattering as seen in FIG. 21 show the increasing amount of polymer as emulsion polymerization proceeds, whereas the decreasing UV signal (at 225 nm) as seen in FIG. 21 shows the conversion of MMA into polyMMA.

Figure 22:
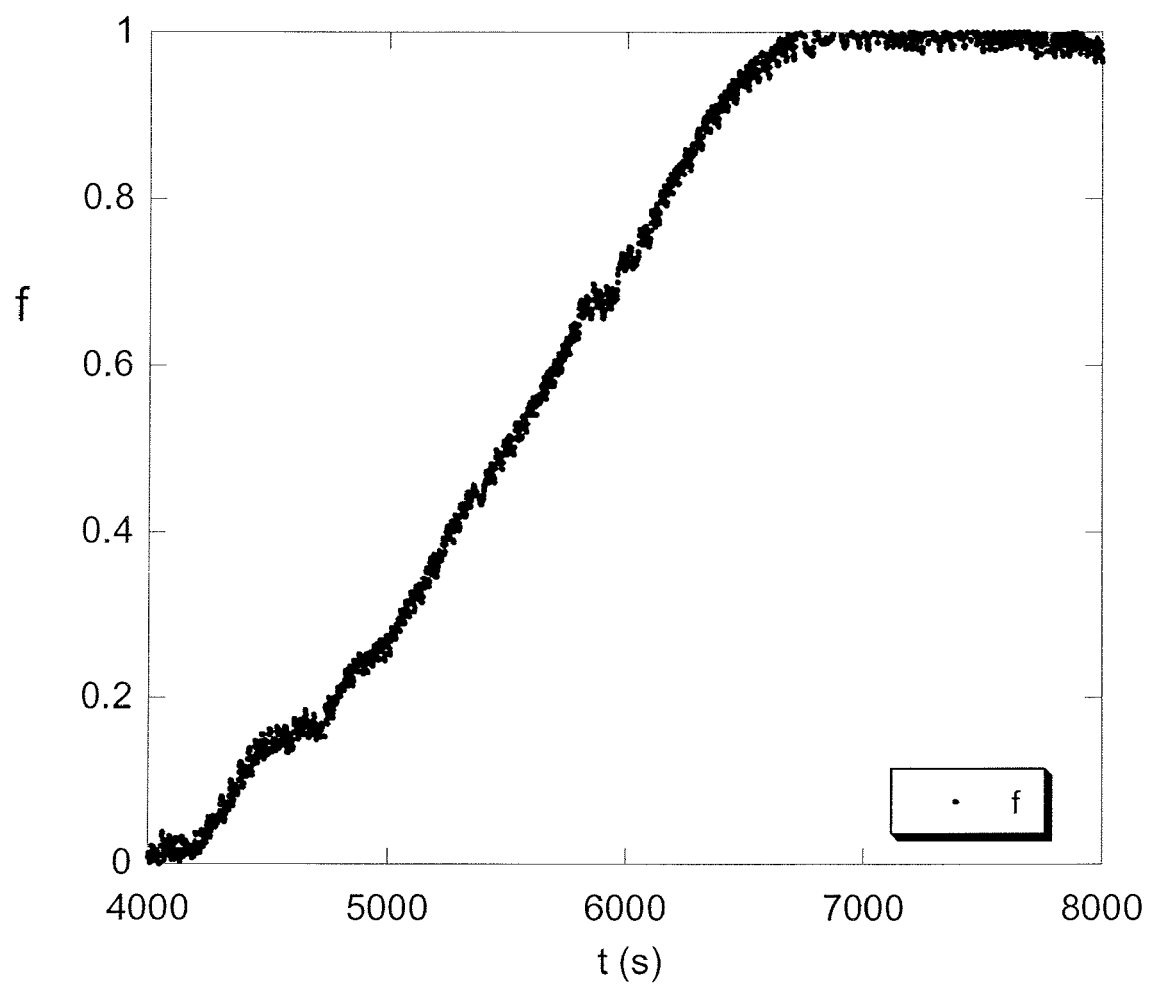
FIG. 22 shows the fractional monomer conversion into polymer vs. time for Reaction #5, computed based on UV data.
Figure 23:
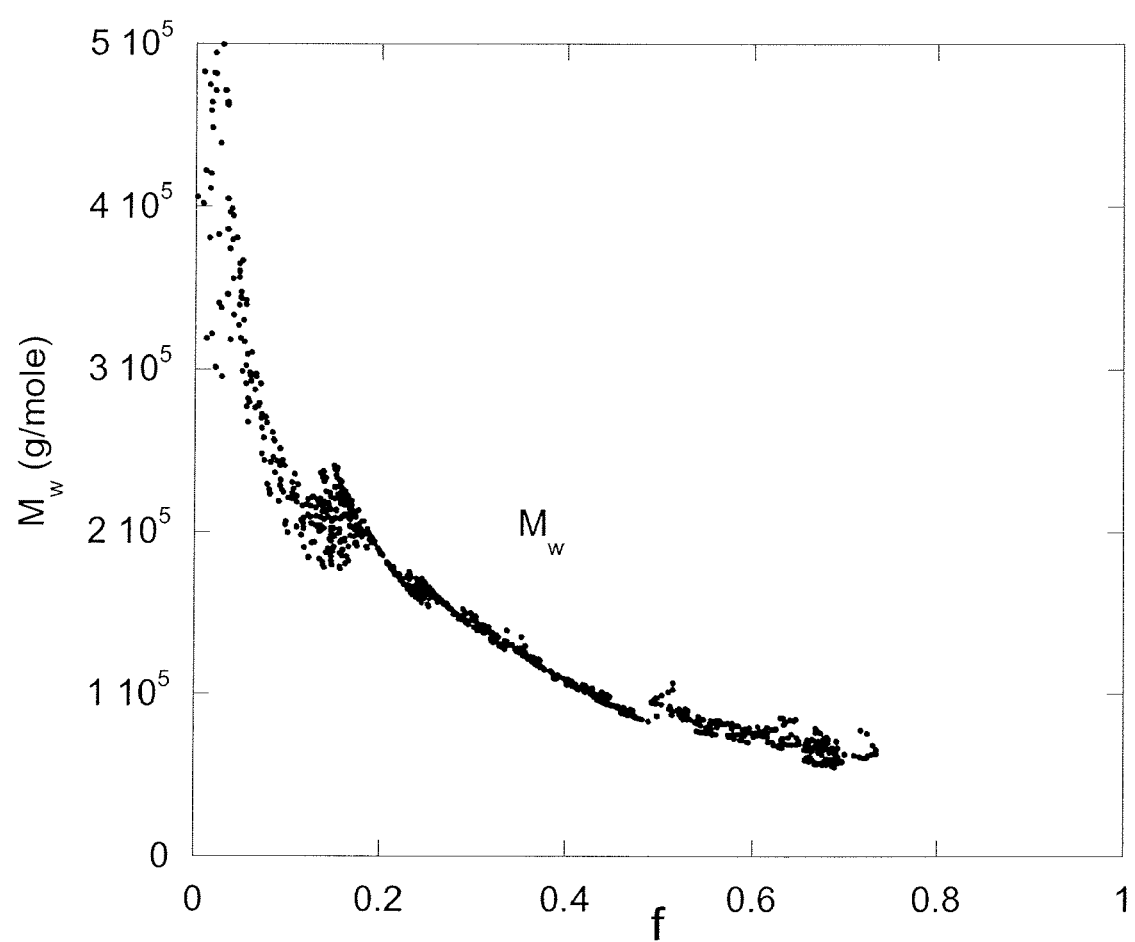
FIG. 23 shows $M_w$, as determined from MALS vs. monomer conversion for Reaction #5.

FIG. 22 shows the fractional monomer conversion into polymer vs. time for Reaction #5, computed based on UV data. FIG. 23 shows $M_w$, as determined from MALS 14 (with dn/dc=0.06 in the factor K) and conversion shown as function of monomer conversion. The decrease in $M_w$ vs. conversion is frequently found in free radical polymerization.

Figure 24:
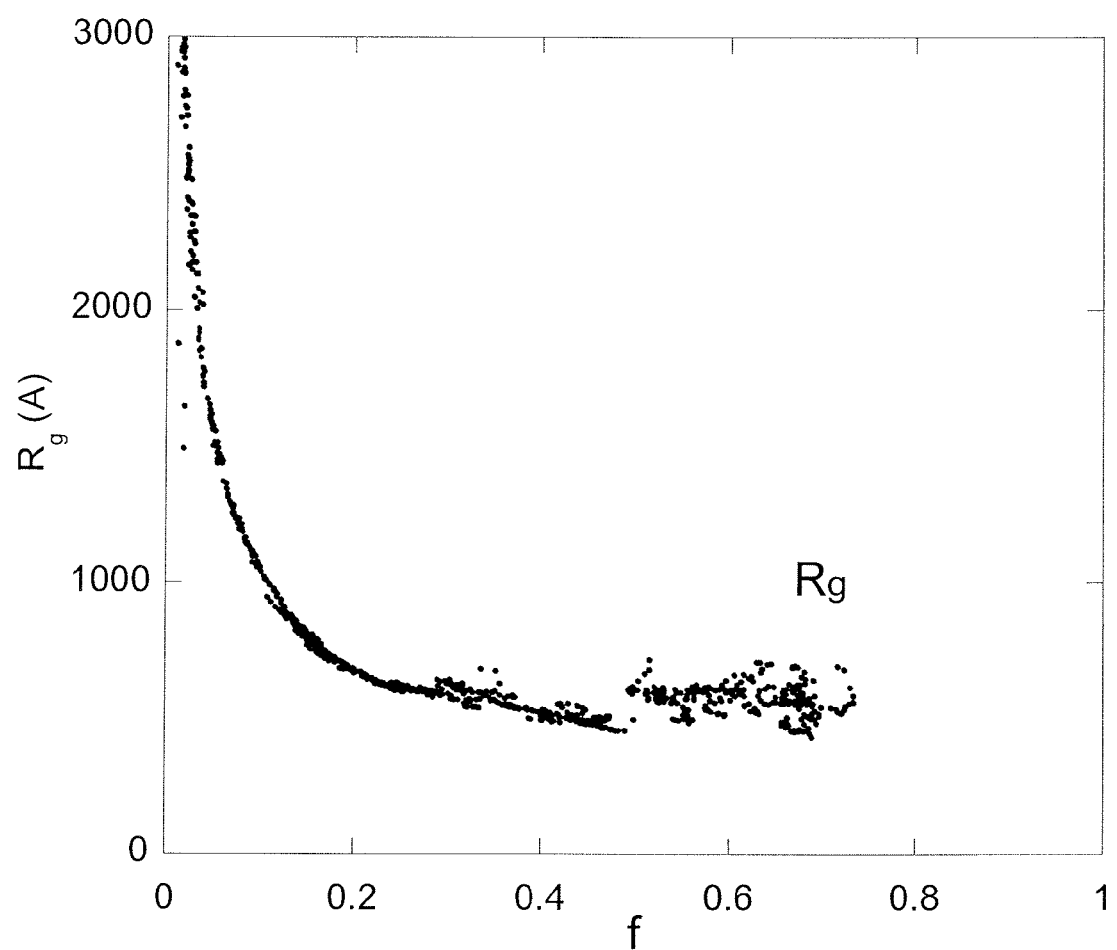
FIG. 24 shows the slope of Kc/I vs $q^2$ allows the radius of gyration vs. conversion for Reaction #5.

The slope of Kc/I vs $q^2$ allows the radius of gyration (in Angstroms) to be computed, shown in FIG. 24 vs. conversion.

Figure 25:
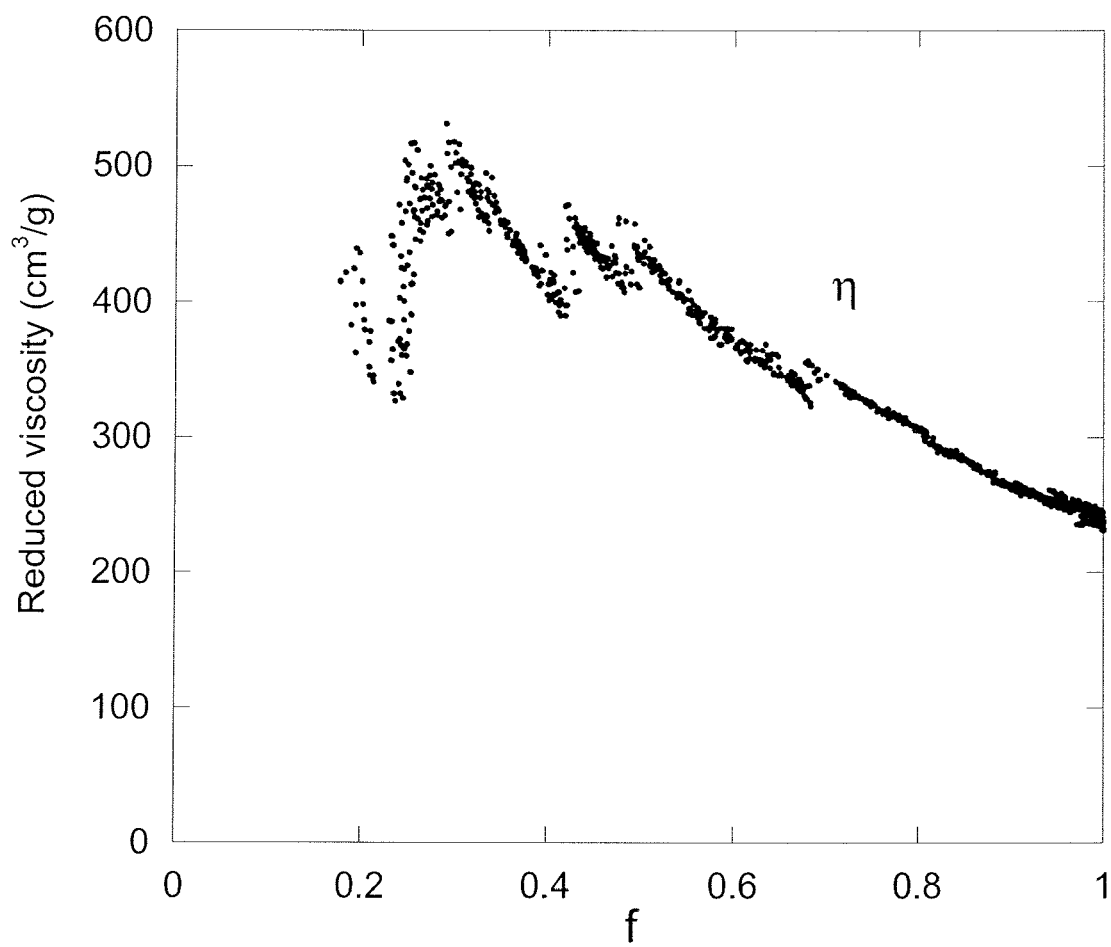
FIG. 25 shows reduced viscosity vs. conversion for Reaction #5.

Reduced viscosity was computed and illustrated vs. conversion in FIG. 25.

Figure 26:
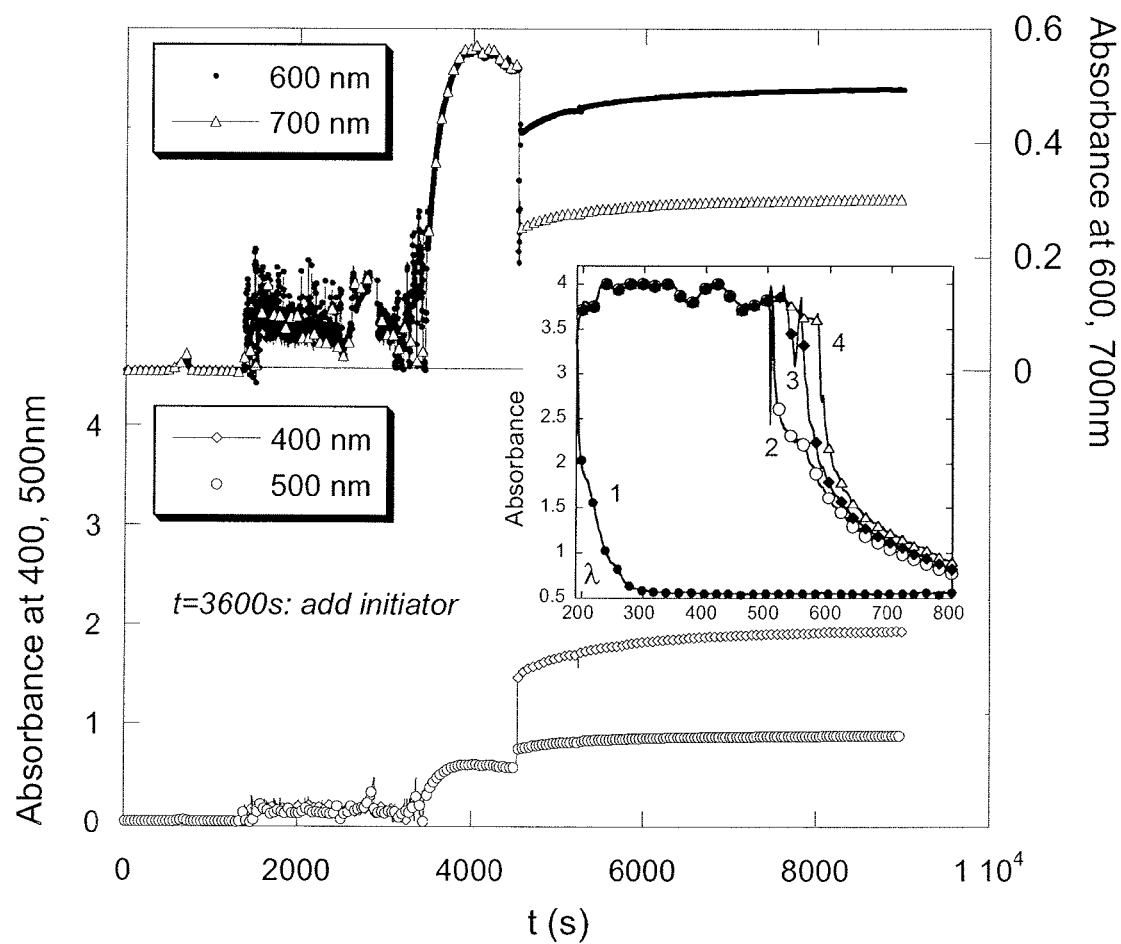
FIG. 26 shows absorbance vs. time for two selected wavelengths for the particle side for Reaction #5.

FIG. 26 shows absorbance vs. time in the particle side for two selected wavelengths. The break after about 5000 s corresponds to a brief failure of the extraction pump and possible air in the system. The inset shows complete visible spectra at selected time points during the reaction. In each case, absorbance at all wavelengths increases as the reaction proceeds and emulsion content in the reactor increases. This is accompanied by a visual change of the reactor contents from nearly clear to a 'milky' white. These data, and others gathered by other instruments, such as DLS 22, will allow particle properties of the emulsions, such as size and number density, to be determined in future work.

The present invention 10 is further useful if the extraction point is from a recirculation loop that is an extension to but forms part of the reaction vessel 11, in which the reaction mixture is continuously driven around this recirculation loop. The extraction points from the recirculation loop can be coincidental or non-coincidental about the loop.

III Polystyrene Latex Manufacture

Figure 27:
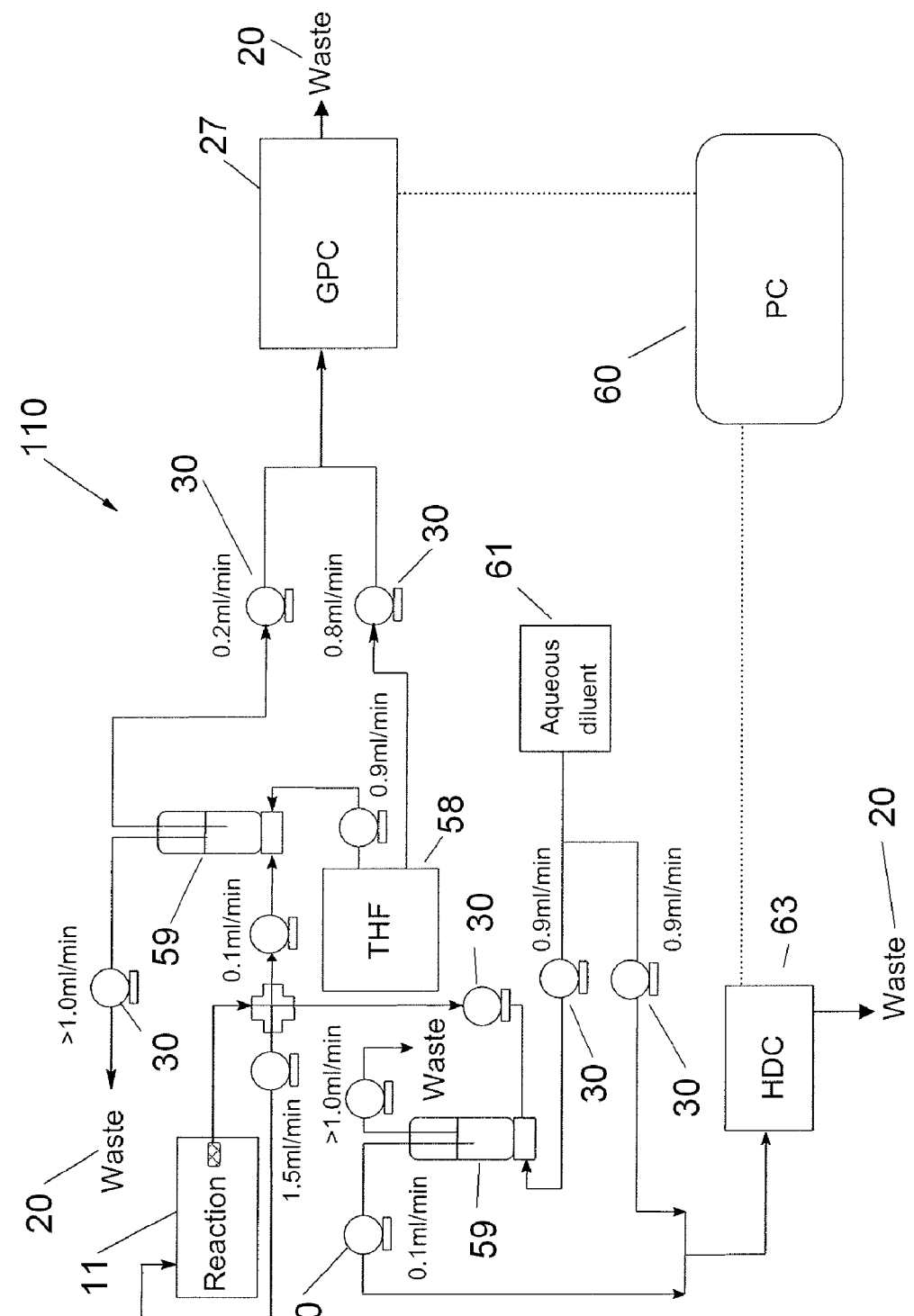
FIG. 27 shows a schematic of the equipment used to monitor the emulsion polymerization of polystyrene.

Description of the experiment as shown in FIG. 27:

Using a cross piece fitted to the recirculation line of a reaction vessel 11 two separate fluid streams are extracted from the reactor. The first stream is diluted in tetrahydrofuran (THF) 58 after which the diluted samples pass continuously through an injection loop of a gel permeation chromatography (GPC) 27 system. The GPC 27 is programmed to inject sample every 6.5 mins from which the polymer molecular weight and distribution is determined at discrete intervals. The second stream is extracted from the reactor using a separate pump 30 and diluted with an aqueous based surfactant 61. This diluted stream is continuously pumped through an injection loop of a hydrodynamic chromatography (HDC) 63 system, with the samples being injected into the system every 6 mins. By using a detector response curve and a calibration curve based on the detector response from a series of accurately sized polystyrene latex samples the particle size and particle size distribution of the reaction samples are continuously monitored. Potassium persulfate was used to initiate the reaction and stearic acid and pH to stabilize the emulsion formed. The reaction mixture was purged before the reaction with nitrogen (and kept under an inert atmosphere throughout the reaction) and the batch volume of approximately 450 ml was stirred throughout by a paddle stirrer at running at approximately 350 rpm.

Conditions:—

Figure 28:
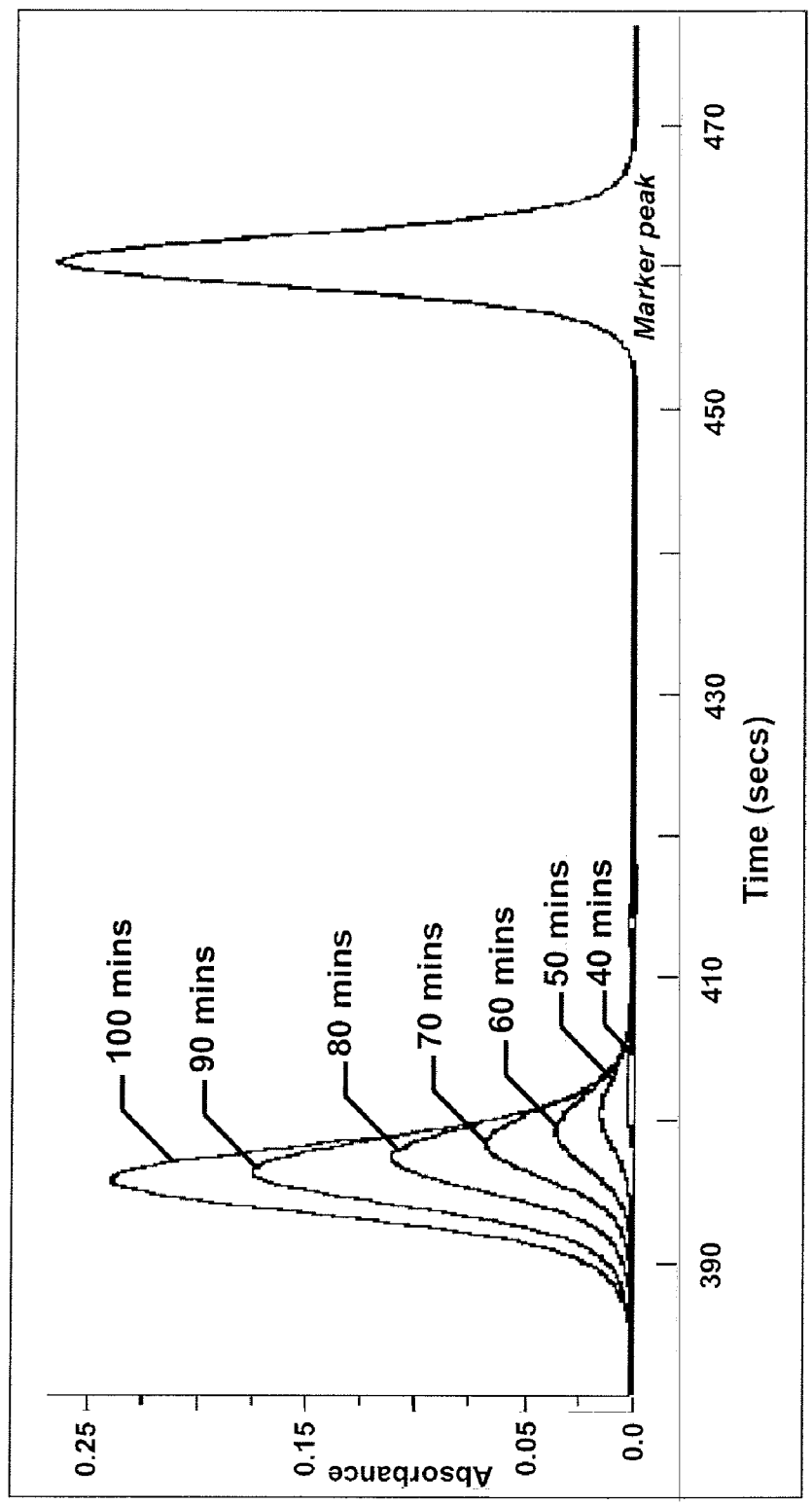
FIG. 28 shows the HDC raw data as monitored by the PL-PSDA.
Figure 29:
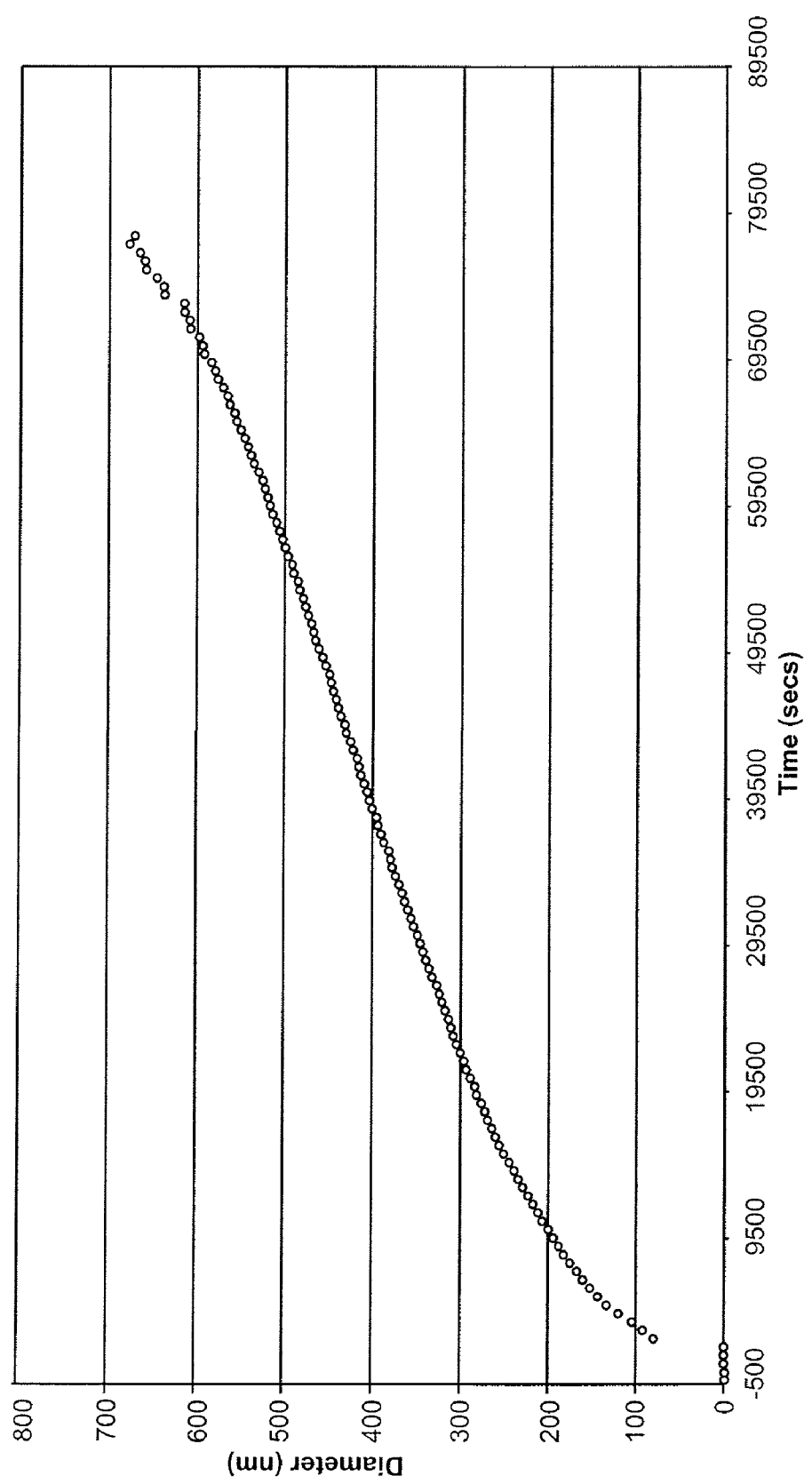
FIG. 29 shows the increase of latex particle size for the Emulsion Polymerization of Styrene.

The reaction mixture entering the recirculation line is filtered through a 100-160 μm glass frit and the material is recycled at 1.5 ml/min. Both of the extracted streams are diluted twice via a low pressure-mixing chamber (LPMC 59) in the first stage and a high pressure mixing chamber (HPMC) in the second, effecting a 50:1 or 100:1 dilution. The GPC 27 system used was a PL-GPC50Plus instrument operating with THF 58 at a flow rate of 1.3 ml/min, 20 μl injection loop and a PL Rapide-L column. The detector used in this system was a dual channel UV detector (Shimadzu) operating two wavelengths 261 nm and 290 nm. The HDC 63 system used was a PL-PSDA unit operating with a propriety HDC eluent at a flow rate of 2.1 ml/min with a type 2 PSDA cartridge. The detector used in this instrument is a single wavelength UV detector operating at 254 nm. The increase in sensitivity as shown in FIG. 28 clearly shows the particle number whereas the move to shorter times shows the increase in particle size. Processing this sample data with the remainder of the data from the reaction gives the particle size for each injection and this data can be plotted against the reaction time as shown below in FIG. 29.

Figure 30:
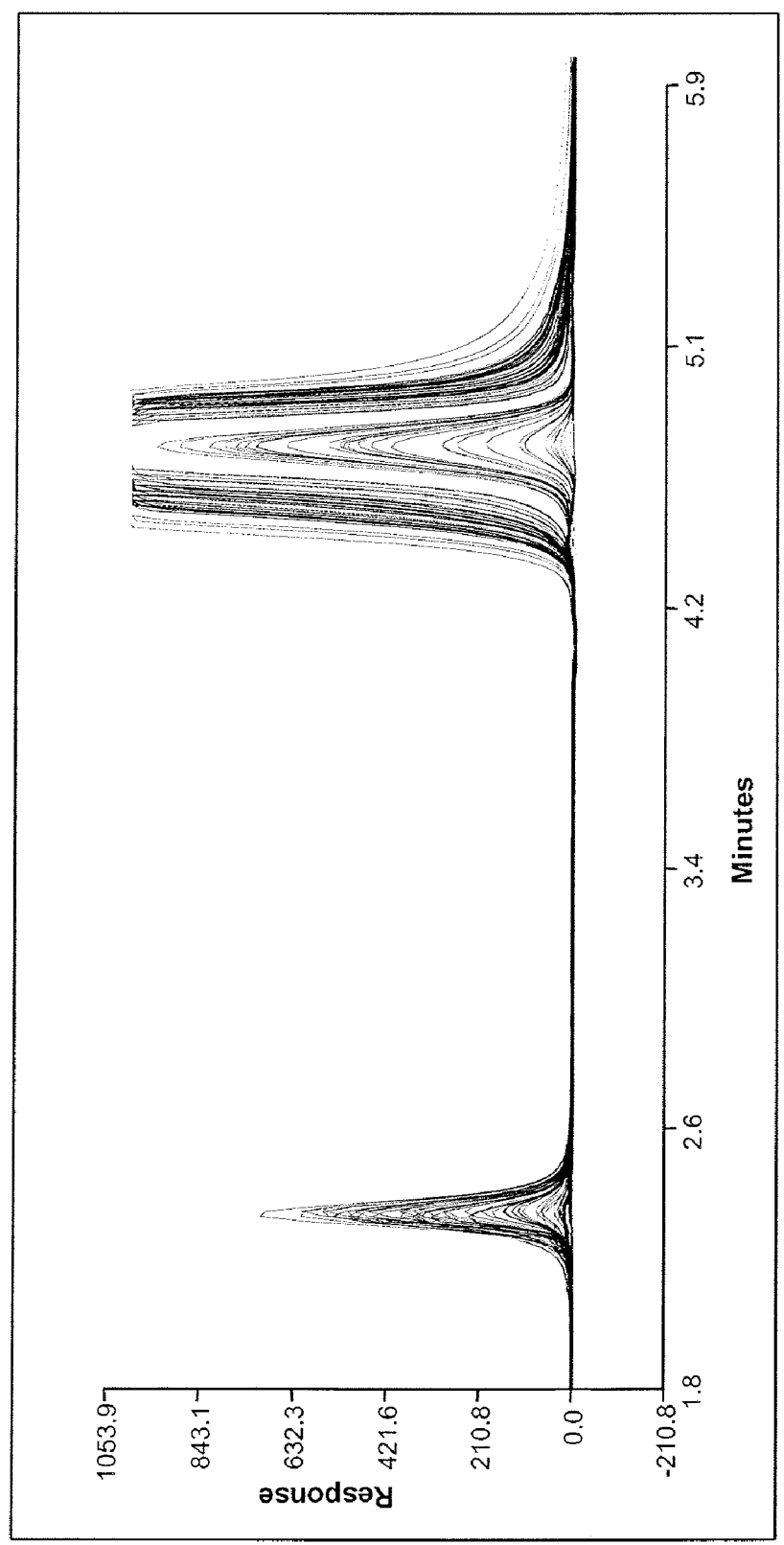
FIG. 30 shows the GPC raw-data obtained from the PL-GPC 50 during the polymerization.
Figure 31:
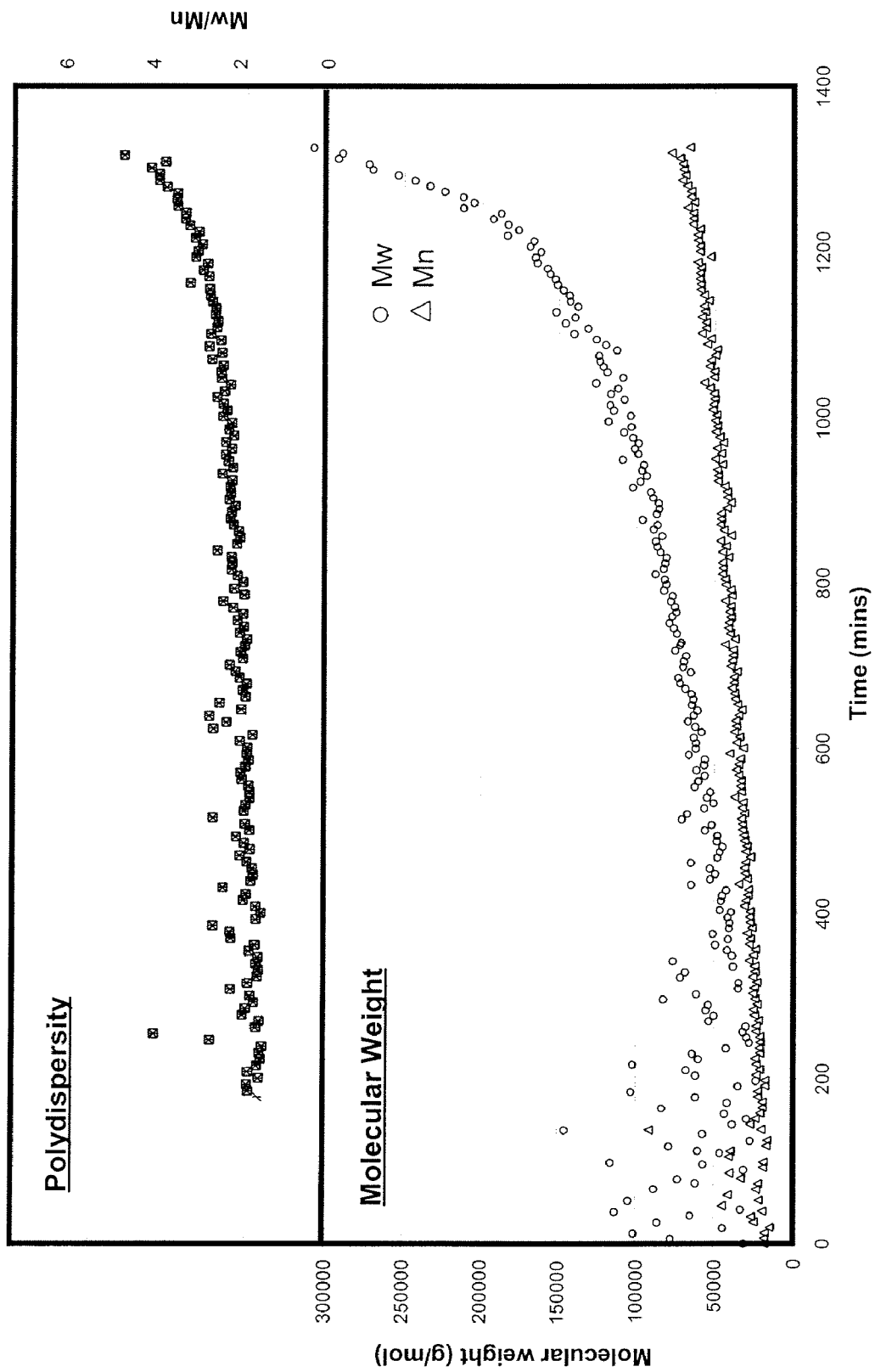
FIG. 31 shows the plots of molecular weight and polydispersity with time.

For the GPC 27, the raw-data as shown in FIGS. 30 and 31 shows a time shift to shorter times giving a direct measure of increased molecular weight throughout the reaction and the increased sensitivity is a direct measure of monomer conversion to polymer, further manipulation of this data yields the basis for kinetic plots.

Figure 36:
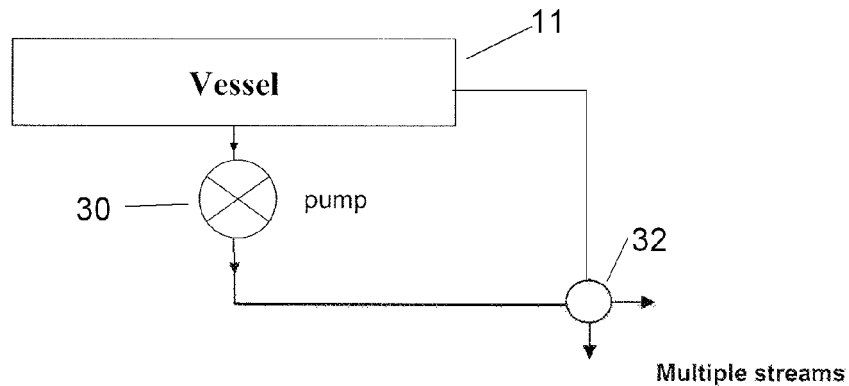
FIG. 36 is a schematic flow chart of another embodiment of the apparatus of the present invention, showing multiple sample streams being extracted from a recirculation loop.
Figure 37:
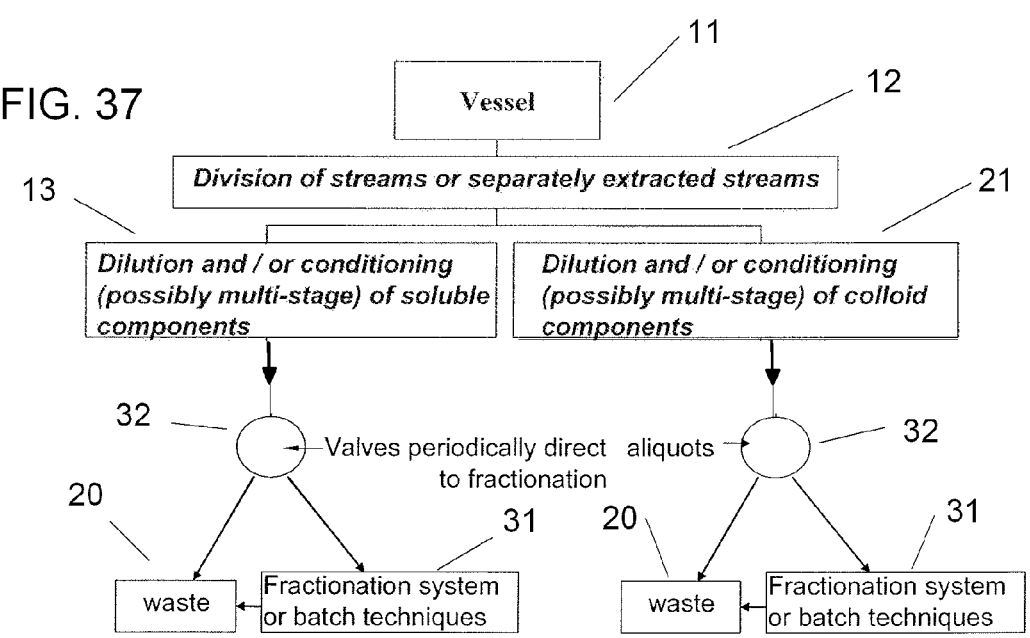
FIG. 37 is a schematic flow chart of another preferred embodiment of the method of the present invention showing direct coupling of extraction dilution to fractionation systems GPC and HDC.

In FIG. 36 tee piece 32 allows two flow streams from a recirculation loop from vessel 11.

IV: Starved Emulsion Polymerization of Styrene

Figure 32:
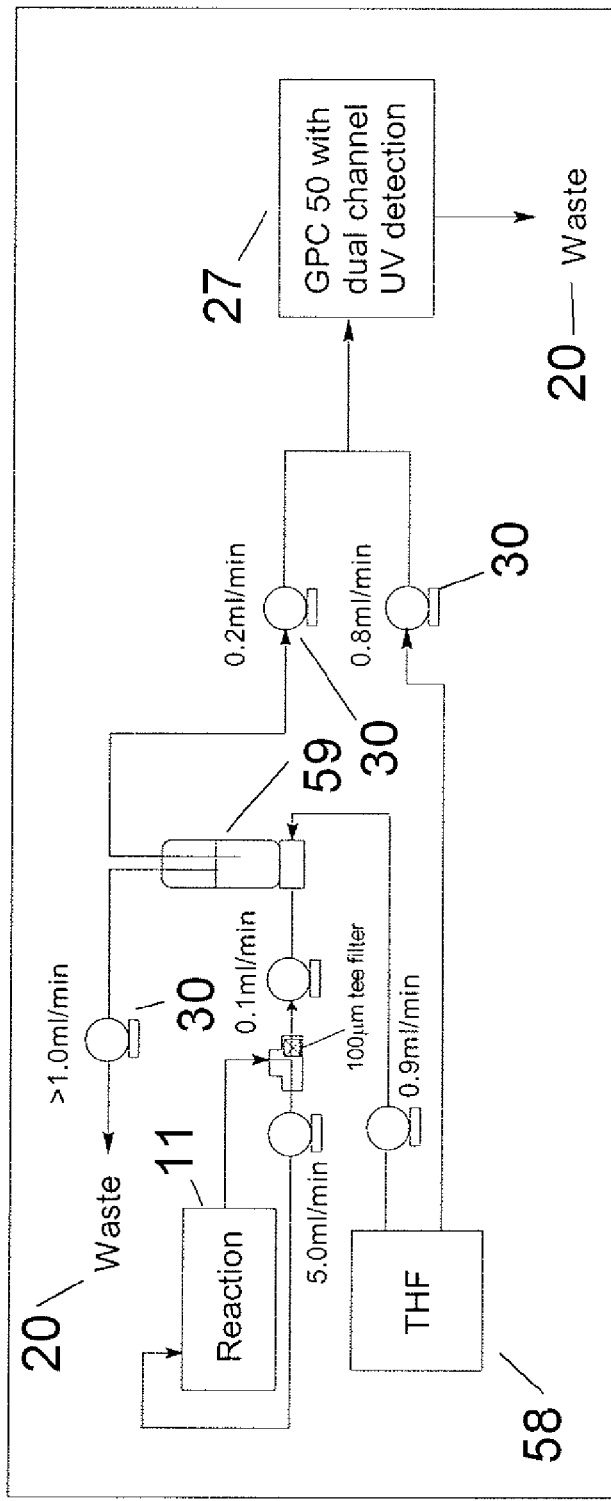
FIG. 32 shows the simple schematic diagram of the equipment used for the starved emulsion polymerization of styrene.

Description of the experiment as shown in FIG. 32:

Using a tee piece fitted to the recirculation line of a reaction vessel a single fluid stream is extracted from the reactor. This stream is diluted in Tetrahydrofuran (THF) 58 after which the diluted samples pass continuously through an injection loop of a gel permeation chromatography (GPC) system 27. The GPC 27 is programmed to inject sample every 6.5 mins from which the polymer molecular weight and distribution is determined at discrete intervals. According to a method taken from Annia Salalzar, Luis M. Gugliotta, Jorge R. Vega and Gregorio R. Meira, Industrial Engineering Chemical Research, Volume 37, pages 3582-3591, 1998, starved emulsion polymerization of styrene of styrene is carried out using tert-dodecyl mercaptam as chain transfer agent, with potassium persulfate initiator, sodium dodecyl sulphate stabiliser and sodium hydrogen carbonate as buffer in deionised water. The water was purged with nitrogen prior to reaction and the reaction maintained under inert atmosphere. The reaction was carried out at an internal temperature of 70° C. with stirring at 270 rpm with a propeller stirrer. The reaction volume was approximately 440 ml. The reaction was initiated by addition of potassium persulfate solution to the preheated soap/water/buffer solution, followed by immediate addition of styrene/CTA solution at 0.2327 ml/min over 420 mins.

Conditions:—

The reaction mixture entering the recirculation line is filtered through a 100-160 μm glass frit and the material is recycled at 1.5 ml/min. The extracted stream is diluted twice via a low pressure-mixing chamber (LPMC) in the first stage and a high pressure mixing chamber (HPMC) in the second, effecting a 50:1 dilution. The GPC system 27 used was a PL-GPC 50Plus instrument operating with THF with a flow rate of 1.3 ml/min, 20 μl injection loop and a PL Rapide-F column. The detector used in this system was a dual channel UV detector (Shimadzu) operating at two wavelengths 261 nm and 290 nm.

Figure 33:
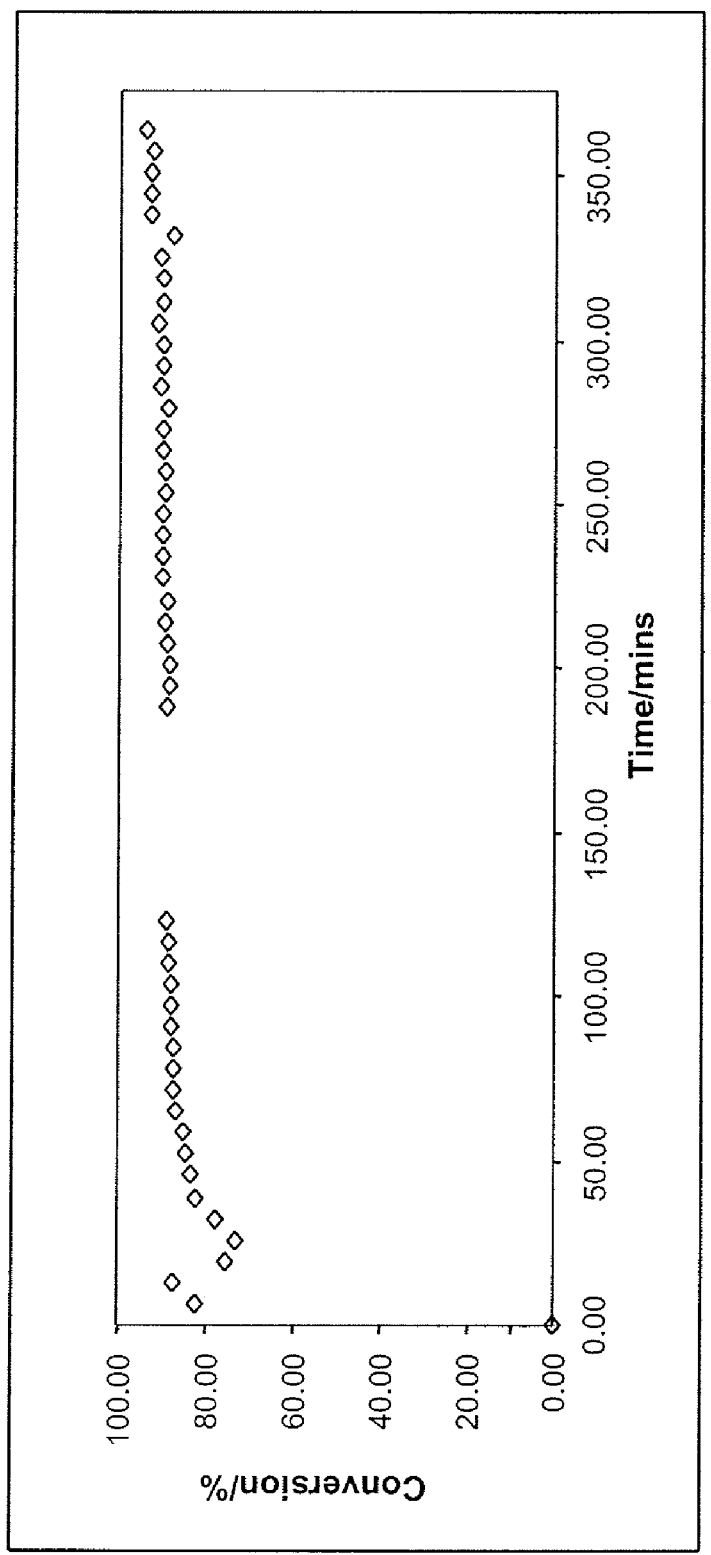
FIG. 33 shows the fractional conversion against time.
Figure 34:
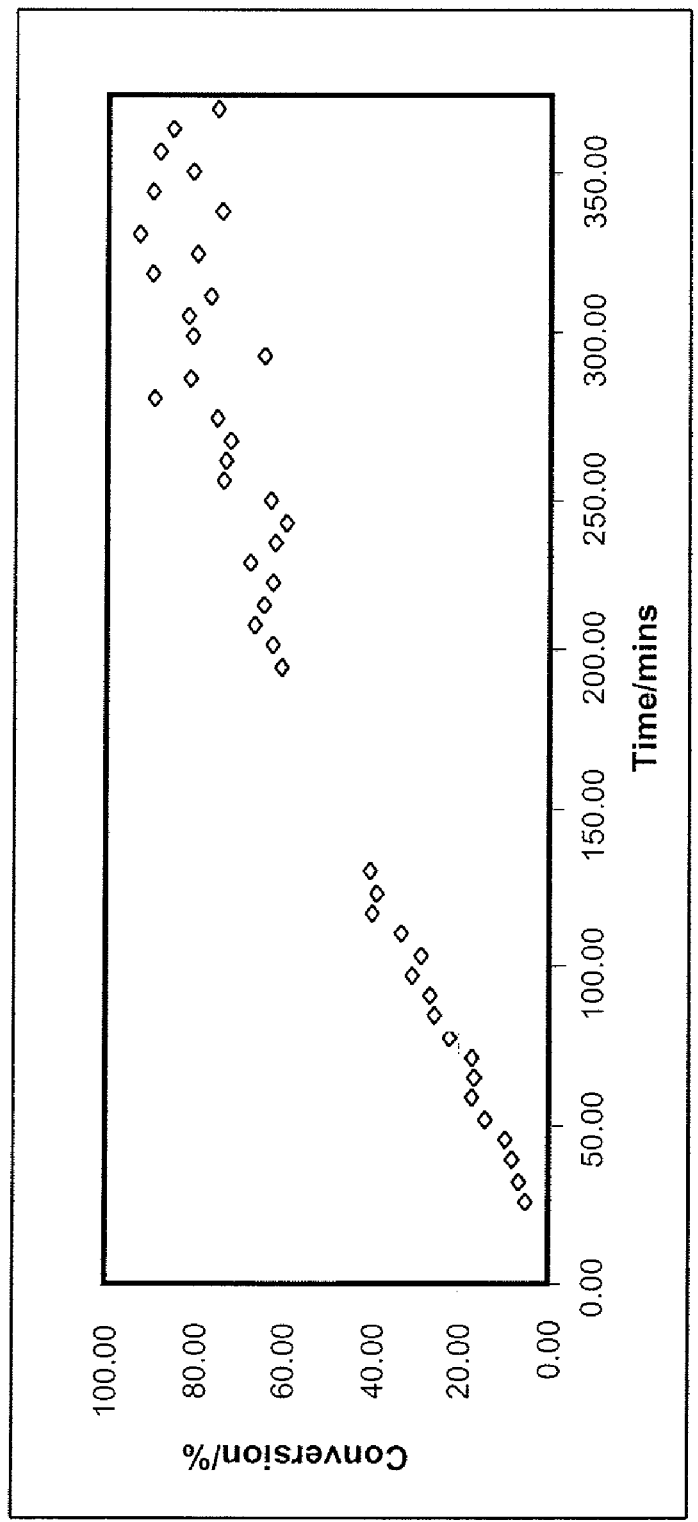
FIG. 34 shows the total conversion against time.
Figure 35:
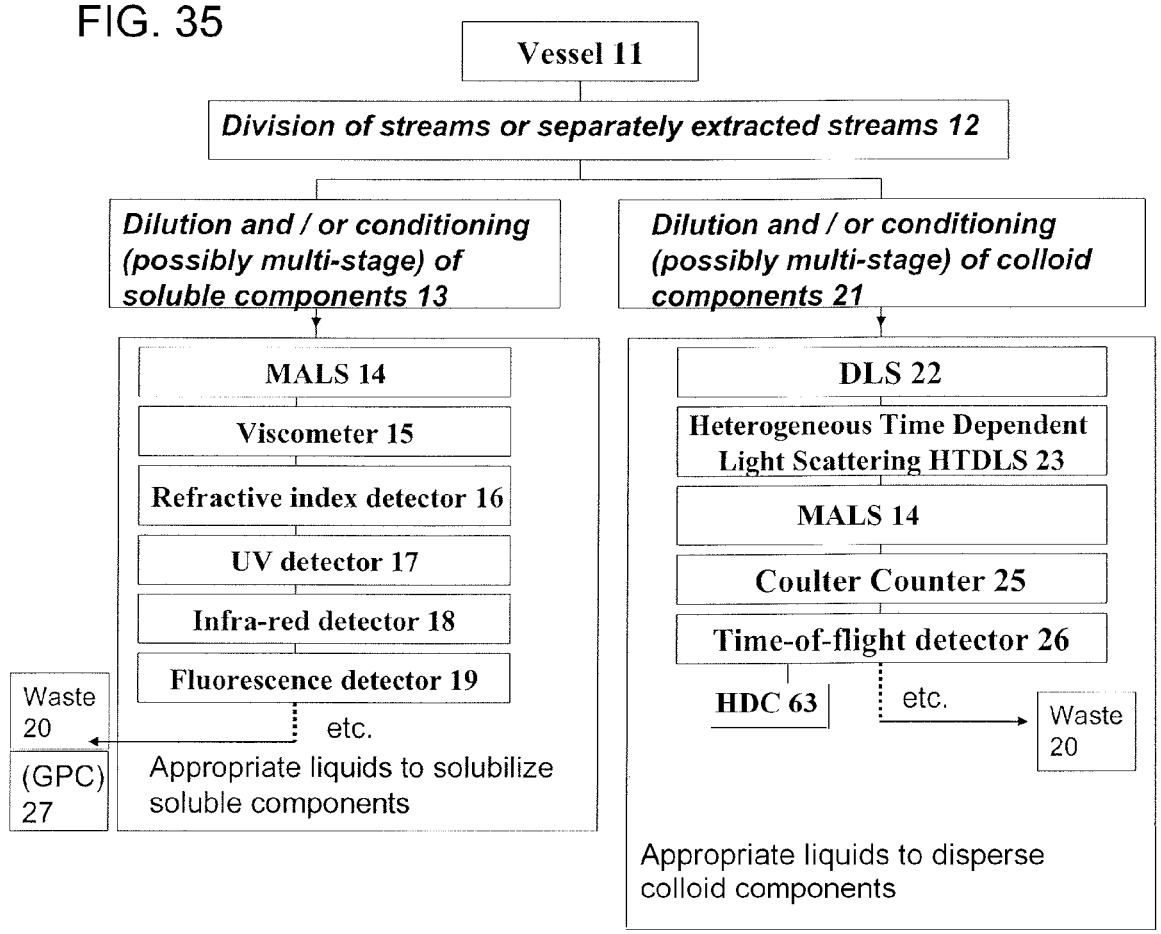
FIG. 35 is a schematic flow chart of another embodiment of the apparatus of the present invention.

Conversion data are derived from the styrene concentration calculated from response at 261 nm and 290 nm, using calibration of the system with samples of styrene in THF at various concentrations as shown in FIGS. 33 and 34.

The data observed is in very close agreement to the literature conversion data, with the low instantaneous levels of styrene enabling reliable conversion calculation on the basis of monomer content. Molecular weight data and conversion by polymer response can also be calculated by this method.

CONCLUSION

The continuous streams of the present invention 10 allow all of the measurements/observations described herein to occur at any moment of the reaction.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims. It will be understood that each of the elements described above, or two or more together, may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of the present invention set forth in the appended claims. The foregoing embodiments are presented by way of example only; the scope of the present invention is to be limited only by the following claims.

While certain novel features of the present invention shown and described below are pointed out in the following claims, the present invention is not intended to be limited to the details specified, since a person of ordinary skill in the relevant art will understand that various omissions, modifications, substitutions and changes in the forms and details of the device illustrated and in its operation may be made without departing in any way from the spirit of the present invention. No feature of the present invention is critical or essential unless it is expressly stated as being "critical" or "essential."

PARTS LIST

The following is a list of parts and materials suitable for use in the present invention:

| | |
|---|---|
| 10 | Apparatus of a first embodiment |
| 11 | Reactor/vessel |
| 12 | Division of streams or separately extracted streams |
| 13 | Dilution and/or conditioning of soluble components |
| 14 | MALS |
| 15 | Viscometer |
| 16 | Refractive index detector |
| 17 | UV detector |
| 18 | Infra-red detector |
| 19 | Fluorescence detector |
| 20 | Waste |
| 21 | Dilution and/or conditioning of colloid components |
| 22 | DLS |
| 23 | Heterogeneous Time Dependent Light Scattering HTDLS |
| 25 | Coulter Counter |
| 26 | Time-of-flight detector |
| 27 | GPC |
| 30 | Pump (e.g. multi-head, peristaltic or separate) |
| 31 | Fractionation system or batch techniques |
| 32 | tee piece |
| 33 | Detectors/detector train |
| 40 | Micro flow controller |
| 41 | Shimadzu pump 1 |
| 42 | Shimadzu pump 2 |
| 43 | Agilent pump |
| 44 | Knauer pump 1 |
| 45 | Q pump 2 |
| 46 | Perist. pump |
| 47 | Waters pump |
| 48 | Eldex pump |
| 49 | Knauer pump 2 |
| 50 | $H_2O$ |
| 51 | Q pump 1 |
| 52 | Stirrer |
| 53 | LPMC1 |
| 54 | LPMC2 |
| 55 | LPMC3 |
| 56 | LPMC4 |
| 58 | THF |
| 59 | low pressure mixing chamber |
| 60 | PC |
| 61 | Aqueous diluent |
| 63 | HDC |
| 70 | Small diameter tube |
| 71 | Medium diameter tube |
| 72 | Large diameter tube |
| 110 | Alternative embodiment of the apparatus |

What is claimed is:

1. A device for determining characteristics of a dispersion of particles and of soluble components of a liquid in a vessel, comprising:
an extracting means for continuously extracting a first stream and a second stream of the liquid from the vessel,
a first dilution/conditioning means for continually diluting and/or conditioning the first stream in one or more stages, whereby the diluted and/or conditioned first stream facilitates characterization of the dispersion of the particles, a second dilution/conditioning means for diluting and/or conditioning the second stream whereby the diluted and/or conditioned second stream facilitates characterization of the soluble components,
a particle characterizing means for characterizing the particles, and
a component characterizing means for characterizing the soluble components.

2. The device of claim 1, wherein the liquid extracted from the vessel is from a polymerization reaction occurring in an emulsion or an inverse emulsion phase.

3. The device of claim 1, further comprising a means for conducting packed column hydrodynamic chromatography on one of the streams.

4. The device of claim 1 further comprising a fractionation means for the soluble component stream, comprising at least one means from the group consisting of GPC, SEC, MALDI-TOF, field flow fractionation, and capillary hydrodynamic fractionation.

5. The device of claim 1, further comprising a single tube for extracting the first stream from the vessel and a dividing means for subsequently dividing the first stream into at least a primary tributary stream and a secondary tributary stream.

6. The device of claim 5, further comprising two or more tributary tubes or capillaries connected to the single tube.

7. The device of claim 1, wherein the second stream further comprises solubilized components.

8. The device of claim 7, wherein the second stream further comprises dissolved components of a polymer reaction from the group consisting of monomers, polymers, and polymer fragments, catalysts, initiators, chelating agents, stabilizing agents, surfactants, salts, and other small (non-polymeric) molecules.

9. The device of claim 7, further comprising subjecting the second stream to at least one characterizing measurement.

10. The device of claim 9, wherein the characterizing measurement is a polymer or monomer characterizing measurement.

11. The device of claim 1, wherein the first stream contains a dispersion of particles.

12. The device of claim 11, wherein the first stream is subjected to at least one characterizing measurement.

13. The device of claim 12, wherein one of the characterizing measurements is a particle characterizing measurement.

14. The device of claim 13, wherein the particle characterizing means includes at least one means from the group consisting of particle size measuring means, particle size distribution determining means, average of the particle size distribution determining means, particle number density measuring means, particle chemical composition determining means, particle shape and morphology determining means, particle structure measuring means.

15. The device of claim 13, wherein the measurement is non-continuous.

16. A device for determining characteristics of a dispersion of particles and of soluble components of a liquid in a vessel in which a reaction, involving polymer and/or dispersed particles, occurs, comprising:
an extracting means for simultaneously extracting a first stream and a second stream of the liquid from the vessel, whereby the extraction is continuous,
a first dilution/conditioning means for continually diluting and/or conditioning the first stream in one or more stages, whereby the diluted and/or conditioned first stream facilitates characterization of the dispersion of the particles, a second dilution/conditioning means for diluting and/or conditioning the second stream whereby the diluted and/or conditioned second stream facilitates characterization of the soluble components related to the reaction in the vessel, such as monomers, comonomers, polymer chains, and fragments of polymers, a particle characterizing means for characterizing the dispersion of the particles, and a component characterizing means for characterizing the soluble components.

17. The device of claim 16, further comprising sample vials in which samples are collected for subsequent measurements of any type from the first stream prior to or subsequent to dilution and/or conditioning or from the second stream prior to or subsequent to dilution and/or conditioning.

18. A method of determining characteristics of a dispersion of particles and of soluble components of a liquid in a vessel, comprising:

continuously extracting a first stream and a second stream of the liquid from the vessel, continually diluting and/or conditioning the first stream in one or more stages, whereby the diluted and/or conditioned first stream facilitates characterization of the dispersion of the particles, diluting and/or conditioning the second stream whereby the diluted and/or conditioned second stream facilitates characterization of the soluble components, characterizing the particles, and characterizing the soluble components.

19. A method of determining characteristics of a dispersion of particles and of soluble components of a liquid in a vessel in which a reaction, involving polymer and/or dispersed particles, occurs, comprising:

simultaneously and continuously extracting a separate first stream and a separate second stream of the liquid from the vessel, continually diluting and/or conditioning the first stream in one or more stages, whereby the diluted and/or conditioned first stream facilitates characterization of the dispersion of the particles, diluting and/or conditioning the second stream whereby the diluted and/or conditioned second stream facilitates characterization of the soluble components related to the reaction in the vessel, such as monomers, comonomers, polymer chains, and fragments of polymers, characterizing the particles, and characterizing the soluble components.

20. The method of claim 19, wherein the liquid in the vessel is a polymerization reaction occurring in an emulsion or inverse emulsion phase.

* * * * *